US009682988B2

(12) United States Patent
Andres et al.

(10) Patent No.: US 9,682,988 B2
(45) Date of Patent: Jun. 20, 2017

(54) SOLID SALT FORM OF α-6-MPEG$_6$-O-HYDROXYCODONE AS OPIOID AGONISTS AND USES THEREOF

(71) Applicant: Nektar Therapeutics, San Francisco, CA (US)

(72) Inventors: Patricia Andres, West Lafayette, IN (US); Yogesh Datar, Indianapolis, IN (US); Ramakrishna Gadiraju, Foster City, CA (US); Bruce Andrew Kowalczyk, Huntsville, AL (US); Gabriel Christian Kuklis, Huntsville, AL (US); Mahmoud Mirmehrabi, Ayer, MA (US); Nicholas Paschalides, Marlborough, MA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/439,473

(22) PCT Filed: Oct. 29, 2013

(86) PCT No.: PCT/US2013/067273
§ 371 (c)(1),
(2) Date: Apr. 29, 2015

(87) PCT Pub. No.: WO2014/070745
PCT Pub. Date: May 8, 2014

(65) Prior Publication Data
US 2015/0284402 A1 Oct. 8, 2015

Related U.S. Application Data

(60) Provisional application No. 61/720,259, filed on Oct. 30, 2012, provisional application No. 61/791,894, filed on Mar. 15, 2013.

(51) Int. Cl.
*C07D 489/04* (2006.01)
*A61K 9/28* (2006.01)
*A61K 31/485* (2006.01)

(52) U.S. Cl.
CPC ............ *C07D 489/04* (2013.01); *A61K 9/284* (2013.01); *A61K 31/485* (2013.01); *C07B 2200/13* (2013.01)

(58) Field of Classification Search
CPC .... C07D 489/04; A61K 9/284; A61K 31/485; C07B 2200/13
See application file for complete search history.

(56) References Cited

U.S. PATENT DOCUMENTS

| | | |
|---|---|---|
| 5,800,334 A | 9/1998 | Wilk |
| 6,096,337 A | 8/2000 | Spireas et al. |
| 6,280,770 B1 | 8/2001 | Pather et al. |
| 6,342,249 B1 | 1/2002 | Wong et al. |
| 7,056,500 B2 | 6/2006 | Bentley et al. |
| 7,488,533 B2 | 2/2009 | Nishi et al. |
| 8,173,666 B2 | 5/2012 | Riggs-Sauthier et al. |
| 8,183,376 B2 | 5/2012 | Cheng et al. |
| 8,440,687 B2 | 5/2013 | Riggs-Sauthier et al. |
| 8,563,726 B2 | 10/2013 | Cheng et al. |
| 8,569,343 B2 | 10/2013 | Riggs-Sauthier et al. |
| 8,575,196 B2 | 11/2013 | Riggs-Sauthier et al. |
| 8,946,285 B2 | 2/2015 | Riggs-Sauthier et al. |
| 8,952,032 B2 | 2/2015 | Riggs-Sauthier et al. |
| 2009/0221766 A1 | 9/2009 | Cheng et al. |
| 2011/0237614 A1 | 9/2011 | Jude-Fishburn et al. |
| 2013/0018190 A1 | 1/2013 | Cheng et al. |
| 2013/0023553 A1 | 1/2013 | Jude-Fishburn et al. |
| 2015/0112069 A1 | 4/2015 | Riggs-Sauthier et al. |

FOREIGN PATENT DOCUMENTS

| | | | |
|---|---|---|---|
| WO | 2011/011543 A1 | 1/2011 | |
| WO | WO2011/011543 | * 1/2011 | ............. A61K 47/48 |

OTHER PUBLICATIONS

English Translation of Eurasian Official Action in Eurasian Patent Application No. 201590853 issued Dec. 10, 2015.
European Communication in European Patent Application No. 13 796 178.5-1452 dated May 31, 2016.
Sheth et al., "Use of Powdered Solutions to Improve the Dissolution Rate of Polythiazide Tablets", Drug Development and Industrial Pharmacy, vol. 16, No. 5, pp. 769-777, (1990).
PCT International Search Report and Written Opinion in corresponding PCT Application No. PCT/US2013/067273 date of mailing Jan. 21, 2014.
PCT International Preliminary Report on Patentability in corresponding PCT Application No. PCT/US2013/067273 date of mailing May 14, 2015.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-1$^{st}$, (Jan. 2003).
NOF Corporation, PEG Derivatives, Phospholipid and Drug Delivery Materials for Pharmaceuticals, 27 pages, Catalogue 2003-2$^{nd}$, (Mar. 2004).

(Continued)

*Primary Examiner* — Sean Basquill

(57) ABSTRACT

Solid forms of certain opioid agonists are provided herein. Methods of preparing the solid forms, methods of using the solid forms, and pharmaceutical compositions comprising the solid forms are also provided herein.

5 Claims, 17 Drawing Sheets

(56) References Cited

OTHER PUBLICATIONS

NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
International Search Report in PCT Application No. PCT/US2013/067273 mailed on Jan. 21, 2014.
English Translation of Chinese Notification of the First Office Action in Patent Application No. 201380056619.8 date of notification Jun. 17, 2016.
English Translation of Eurasian Office Action in Patent Application No. 201590853/28 date Aug. 26, 2016.

* cited by examiner

SOLID SALT FORM OF α-6-MPEG$_6$-O-HYDROXYCODONE AS OPIOID AGONISTS AND USES THEREOF

CROSS REFERENCE TO RELATED APPLICATIONS

This application is a 35 U.S.C. 371 application of International Application No. PCT/US2013/067273, filed Oct. 29, 2013, designating the United States, which claims the benefit of priority under 35 U.S.C. §119(e) to U.S. Provisional Patent Application Ser. No. 61/720,259, filed on Oct. 30, 2012, and U.S. Provisional Patent Application Ser. No. 61/791,894, filed on Mar. 15, 2013, the disclosures of which are incorporated by reference in their entireties.

This application claims the benefit of priority under 35 U.S.C. §119(e) to U.S. Provisional Patent Application Ser. No. 61/720,259, filed on Oct. 30, 2012, and U.S. Provisional Patent Application Ser. No. 61/791,894, filed on Mar. 15, 2013, the disclosures of which are incorporated by reference in their entireties.

Solid forms of certain opioid agonists are provided herein. Methods of preparing the solid forms, methods of using the solid forms, and pharmaceutical compositions comprising the solid forms are also provided herein.

Pain is the most common side effect for which patients seek medical attention. Opioid analgesics have long been considered the best option for effectively treating pain. While useful to manage and treat pain, many opioids are associated with serious central nervous system (CNS) side effects. Such side effects include, but are not limited to, respiratory depression, sedation, and abuse liability. The risk of abuse and overdose is high, as several U.S. agencies, including the Center for Disease Control (CDC), the Food and Drug Administration, and the White House, consider prescription opioid analgesics to be at the center of a public health crisis in the United States. CDC Mortality and Morbidity Report (Jan. 13, 2012), vol. 61, no. 1, pp. 10-13.

In an attempt to address the CNS side effects associated with opioids, certain novel opioid agonists have been developed. U.S. Patent Application Publication No. 2010/0048602; U.S. Patent Application Publication No. 2011/0237614; U.S. Patent Application Publication No. 2012/0184581, and U.S. Patent Application Publication No. 2013/0023553. These compounds are believed to, among other things, maintain analgesic properties while entering the CNS at a slower rate than existing opioids. Particularly, these compounds are believed to act as mu opioid agonists.

In part of moving these opioid agonists forward as a drug candidate, it is important to understand if such compounds exist in solid forms. A solid form of a drug substance is often advantageous when developing and formulating a drug product. At the very least, a solid form can aid in the ease of handling of the drug product and in certain instances provide advantageous properties over the non-solid form. Often times, for example, the stability of a solid form is improved over the liquid form. Currently, α-6-mPEG$_6$-O-hydroxycodone in the freebase form exists as a viscous liquid and no solid form has been prepared to date. While the liquid form may be usable, it would clearly be desirable to have a solid form of α-6-mPEG$_6$-O-hydroxycodone available as those forms may have physicochemical properties that may be used advantageously in pharmaceutical processing and in pharmaceutical compositions.

In certain embodiments, provided herein are one or more solid salt forms of α-6-mPEG$_6$-O-hydroxycodone.

In certain embodiments, provided herein are methods for preparing one or more solid salt forms of α-6-mPEG$_6$-O-hydroxycodone.

In certain embodiments, a pharmaceutical composition is provided, wherein the pharmaceutical composition comprises at least one solid salt form of α-6-mPEG$_6$-O-hydroxycodone and optionally at least one pharmaceutically acceptable excipient.

In certain embodiments, a method of preparing a free flowing solid comprising an opioid agonist is provided.

In certain embodiments, a method of treating pain in a patient is provided, the method comprising administering a solid salt form of α-6-mPEG$_6$-O-hydroxycodone.

In certain embodiments, a method of treating pain in a patient is provided, the method comprising administering a pharmaceutical composition comprising at least one solid salt form of α-6-mPEG$_6$-O-hydroxycodone and optionally at least one pharmaceutically acceptable excipient.

Figure 1:
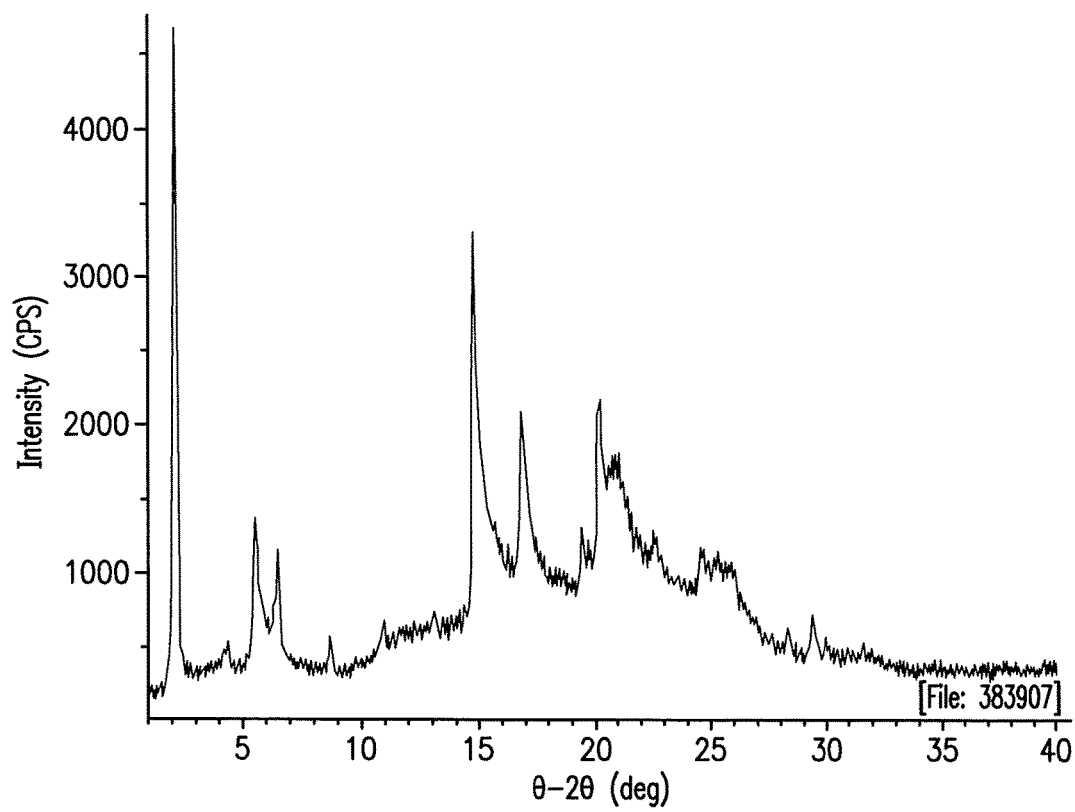
FIG. 1 is an XRPD (X-Ray Powder Diffraction) pattern for the solid α-6-mPEG$_6$-O-hydroxycodone phosphate salt prepared according to Example 1.

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood to one of ordinary skill in the art to which this disclosure belongs.

As used herein, the term "α-6-mPEG$_6$-O-hydroxycodone," "PEG$_6$-Oxycodol," and "mPEG$_6$-O-hydroxycodone" are used to refer to a compound of the formula:

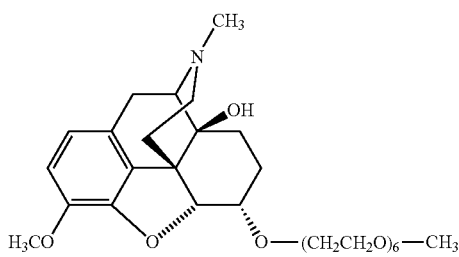

which, unless otherwise stated or apparent from the context in which it is used, means in its free base form. A salt of α-6-mPEG$_6$-O-hydroxycodone, as understood by one of skill in the art, is an ionic form of the α-6-mPEG$_6$-O-hydroxycodone that exists with a counterion produced from, in this case, an acid. The counterion produced from the acid is variously referred to herein as an "acid counterion" or "counterion." When, for example, the acid counterion is phosphoric acid, the α-6-mPEG$_6$-O-hydroxycodone salt is a phosphate salt or phosphoric acid salt. When, for example, the acid counterion is D-tartaric acid, the α-6-mPEG$_6$-O-hydroxycodone salt is a D-tartaric acid salt or a D-tartrate salt.

While not intending to be limited by any theory or mechanism, it is believed that an ionic species of α-6-mPEG$_6$-O-hydroxycodone may include species where the nitrogen accepts a proton, having the formula:

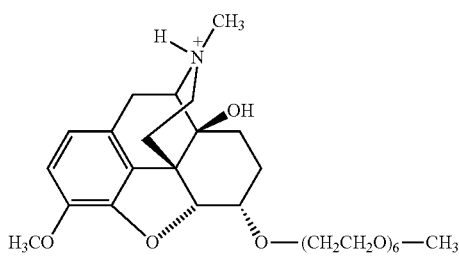

As used herein, and unless otherwise specified, the terms "about" and "approximately," when used in connection with doses, amounts, or weight percent of ingredients of a composition or a dosage from, mean a dose, amount, or weight percent that is recognized by those of ordinary skill in the art to provide a pharmacological effect equivalent to that obtained from the specified dose, amount, or weight percent. Specifically, the terms "about" and "approximately," when use in this context, contemplate a dose, amount, or weight percent within 15%, within 10%, within 5%, within 4%, within 3%, within 2%, within 1%, or within 0.5% of the specified dose, amount, or weight percent.

As used herein, and unless otherwise specified, the terms "about" and "approximately," when used in connection with a numeric value or range of values which is provided to described a particular solid form, e.g., a specific temperature or temperature range, such as, for example, that describing a melting, dehydration, desolvation or glass transition; a mass change, such as, for example, a mass change as a function of temperature or humidity; a solvent or water content, in terms of, for example, mass or a percentage; or a peak position, such as for example, in analysis by, for example, differential scanning calorimetry (DSC), thermogravimetric analysis (TGA), or powder X-ray powder diffraction (XRPD); indicate that the value or range of values may deviate to an extent deemed reasonable to one of ordinary skill in the art while still describing the particular solid form. Specifically the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2%, or 0.1% of the recited value or range while still describing the particular solid form.

The term "solid form" refers to a form of a chemical compound, including a salt of that compound (e.g. a solid salt form), that exists as a solid. Solid forms may include, for example, crystalline forms, disordered crystalline forms, mesophasic forms, and amorphous forms.

The term "amorphous" or "amorphous form" is intended to mean that the substance, component, or product in question is not substantially crystalline as determined, for example, by XRPD or where the substance, component, or product in question, for example is not birefringent when viewed microscopically. In certain embodiments, a sample comprising an amorphous form of a substance may be substantially free of other amorphous forms and/or crystalline forms.

The term "crystalline form" or "crystal form" refers to a crystalline solid form of a chemical compound, including, but not limited to, a single-component or multiple-component crystal form, e.g., a polymorph of a compound; or a solvate, a hydrate, a clathrate, a cocrystal, a salt of a compound, disordered crystalline forms, or a polymorph thereof. "Crystal forms" and related terms herein refer to the various crystalline modifications of a given substance, including, but not limited to, polymorphs, solvates, hydrates, co-crystals, and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal countermolecules, desolvation, dehydration, rapid evaporation, rapid cooling, slow cooling, vapor diffusion, sublimation, reaction crystallization, antisolvent addition, grinding and solvent-drop grinding.

The term "mesophasic" or "mesophasic form" refers to a form of a chemical compound that in an intermediate state between solid and liquid.

The term "disordered crystalline" refers to a solid form that has characteristics of a crystal but lacks the long range order of a purely crystalline material.

Techniques for characterizing solid forms and amorphous forms include, but are not limited to, thermal gravimetric analysis (TGA), melting point analysis, differential scanning calorimetry, vibrational spectroscopy, e.g. infrared (IR) and Raman spectroscopy, solid state NMR, X-ray powder diffraction, optical microscopy, hot stage optical microscopy, scanning electron microscopy (SEM), electron crystallography and quantitative analysis, particle size analysis (PSA), surface area analysis, solubility studies, and dissolution studies.

As used herein and unless otherwise indicated, the term "hydrate" means a compound or salt thereof, further including a stoichiometric or non-stoichiometric amount of water bound by non-covalent intermolecular forces. As used herein and unless otherwise indicated, the term "solvate" means a solvate formed from the association of one or more solvent molecules to a compound provided herein. The term "solvate" includes hydrates (e.g. monohydrate, dihydrate, trihydrate, tetrahydrate, and the like).

The term "pharmaceutically acceptable excipient" refers to a pharmaceutically-acceptable material, composition, or vehicle, such as a liquid or solid filler, diluents, solvent, or encapsulating material. In certain embodiments, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21$^{st}$ ed.; Lippincott Williams & Wilkins: Philadelphia, Pa., 2005; *Handbook of Pharmaceutical Excipients*, 6$^{th}$ ed.; Rowe et al., Eds.; The Pharmaceutical Press and the American Pharmaceutical Association: 2009, *Handbook of Pharmaceutical Additives*, 3$^{rd}$ ed.; Ash and Ash Eds.; Gower Publishing Company: 2007; *Pharmaceutical Preformulation and Formulation*, 2$^{nd}$ ed.; Gibson Ed.; CRC Press LLC: Boca Raton, Fla., 2009.

The term "polymorph" or "polymorphic form" refers to one of two or more crystal forms that comprise the same molecule, molecules or ions. Different polymorphs may have different physical properties such as, for example, melting temperatures, heats of fusion, solubilities, dissolution rates, and/or vibrational spectra as a result of the arrangement or conformation of the molecules or molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g. tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs).

As used herein and unless otherwise indicated, the term "stereomerically pure" means a composition that comprises one stereoisomer of a compound and is substantially free of other stereoisomers of that compound. In certain embodiments stereomerically pure α-6-mPEG$_6$-O-hydroxycodone or salt thereof (including solid salt forms) is provided herein that is substantially free of other stereoisomers including, for example, β-6-mPEG$_6$-O-hydroxycodone or salts thereof. In certain embodiments, a stereomerically pure compound or salt thereof comprises greater than about 80 percent by weight of one stereoisomer of the compound and less than about 20 percent by weight of other stereoisomers of the compound, greater than about 90 percent by weight of one stereoisomer of the compound and less than about 100 percent by weight of other stereoisomers of the compound, greater than about 95 percent by weight of one stereoisomer of the compound and less than about 5 percent by weight of other stereoisomers of the compound, greater than about 97 percent by weight of one stereoisomer of the compound and less than about 3 percent by weight of other stereoisomers of the compound, greater than about 99 percent by weight of one stereoisomer of the compound and less than about 1 percent by weight of other stereoisomers of the compound. In certain embodiments, the term "stereomerically pure" α-6-mPEG$_6$-O-hydroxycodone means that the compound is made up of approximately 100% by weight of α-6-mPEG$_6$-O-hydroxycodone. The above percentages are based on the total amount of combined stereoisomers of the compound.

As used herein, a solid form that is "pure," i.e., substantially free of other solid forms, contains less than about 15 percent by weight of one or more other solid forms, less than about 10 percent by weight of one or more other solid forms, less than about 5 percent by weight of one or more other solid forms, less than about 3 percent by weight of one or more other solid forms, less than about 1 percent by weight of one or more other solid forms, or less than about 0.5 percent by weight of one or more other solid forms. In certain embodiments, as used herein, "substantially pure" α-6-mPEG$_6$-O-hydroxycodone salt or a solid form thereof can mean free of organic impurities, for example, unreacted precursors and side products or oxidative degradation products that might be present in the process for preparing α-6-mPEG$_6$-O-hydroxycodone free base, or storing α-6-mPEG$_6$-O-hydroxycodone free base. Organic impurities can include, for example, α-6-hydroxycodone, α-6-hydroxycodone conjugated to 3, 4, 5, 7, 8, 9, or 10 polyethylene glycol subunits (i.e. ethylene oxide monomers), and so forth. An oxidative degradation product of α-6-mPEG$_6$-O-hydroxycodone free base can, for instance, be the N-oxide of the free base. As such, a "substantially pure" solid form of α-6-mPEG$_6$-O-hydroxycodone salt may comprise, in certain embodiments, less than about 10%, 5%, 3%, 2%, 1%, 0.75%, 0.5%, 0.25%, or 0.1% by weight of one or more other solid forms of the compound and/or other chemical compounds. In certain embodiments, a solid form of α-6-mPEG$_6$-O-hydroxycodone salt that is substantially pure is substantially free of one or more salt forms, amorphous forms, and/or other chemical compounds.

The term "patient," "subject," and "individual" as used herein are interchangeable and refer to a living organism suffering from or prone to a condition that can be prevented or treated by administration of a compound of the invention as described herein, and includes both humans and animals. Such a condition includes pain, for example, nociceptive pain.

The terms "treat," "treating," and "treatment," as used herein with reference to α-6-mPEG$_6$-O-hydroxycodone and solid salt forms thereof, are meant to include alleviation of a condition or symptoms of a condition, for example alleviation of pain or abrogating pain.

The terms "prevent," "preventing," and "prevention," as used herein with reference to α-6-mPEG$_6$-O-hydroxycodone and solid salt forms thereof, are meant to include decreasing the likelihood of occurrence of a condition or symptoms of a condition, for example decreasing the likelihood of occurrence of pain or decreasing the severity of pain.

The term "therapeutically effective amount" is meant to include the amount of α-6-mPEG$_6$-O-hydroxycodone including solid salts forms thereof that, when administered to a subject, is sufficient to prevent pain to some extent, reduce pain, to treat pain, and/or alleviate pain, in the subject when administered.

In certain embodiments, a solid salt form of an α-6-mPEG$_6$-O-hydroxycodone is provided. In certain embodiments, the solid salt form of α-6-mPEG$_6$-O-hydroxycodone is a disordered crystalline form. In certain embodiments, the solid salt form of α-6-mPEG$_6$-O-hydroxycodone is a crystalline form. In certain embodiments, the solid salt form of α-6-mPEG$_6$-O-hydroxycodone is a mesophasic form. In certain embodiments, the solid salt form is an α-6-mPEG$_6$-O-hydroxycodone phosphate salt. In certain embodiments, the solid salt form is an α-6-mPEG$_6$-O-hydroxycodone D-tartrate salt.

In certain embodiments, an α-6-mPEG$_6$-O-hydroxycodone phosphate salt is provided. In certain embodiments, a solid salt form of an α-6-mPEG$_6$-O-hydroxycodone phosphate salt is provided. In certain embodiments, the solid salt form of an α-6-mPEG$_6$-O-hydroxycodone phosphate salt is a mesophasic form. In certain embodiments, the solid salt form of an α-6-mPEG$_6$-O-hydroxycodone phosphate salt is in a disordered crystalline form. In certain embodiments, the solid salt form of an α-6-mPEG$_6$-O-hydroxycodone phosphate salt is in a crystalline form.

In certain embodiments, the solid α-6-mPEG$_6$-O-hydroxycodone phosphate salt form is a monophosphate salt. That is, the phosphate anion and α-mPEG$_6$-O-hydroxycodone cation are present in about a 1:1 ratio.

In certain embodiments, the solid α-6-mPEG$_6$-O-hydroxycodone salt form provided herein (e.g. a phosphate or D-tartrate salt) in a substantially pure form. For example, in certain embodiments a solid α-6-mPEG$_6$-O-hydroxycodone salt can have a purity of at least about 84%, at least about 85%, at least about 90%, at least about 95%, at least about 97%, at least about 98%, at least about 99%, at least about 99.2%, at least about 99.5%, at least about 99.6%, at least about 99.7% or at least about 99.8% by weight of a single solid form, the remainder of the total weight which may be other solid forms and/or other compounds (such as, for example, an oxidative degradation product).

In certain embodiments, the solid form of α-6-mPEG$_6$-O-hydroxycodone phosphate salt has X-ray powder diffraction two theta peak values substantially similar to those of FIG. 1.

Figure 16:
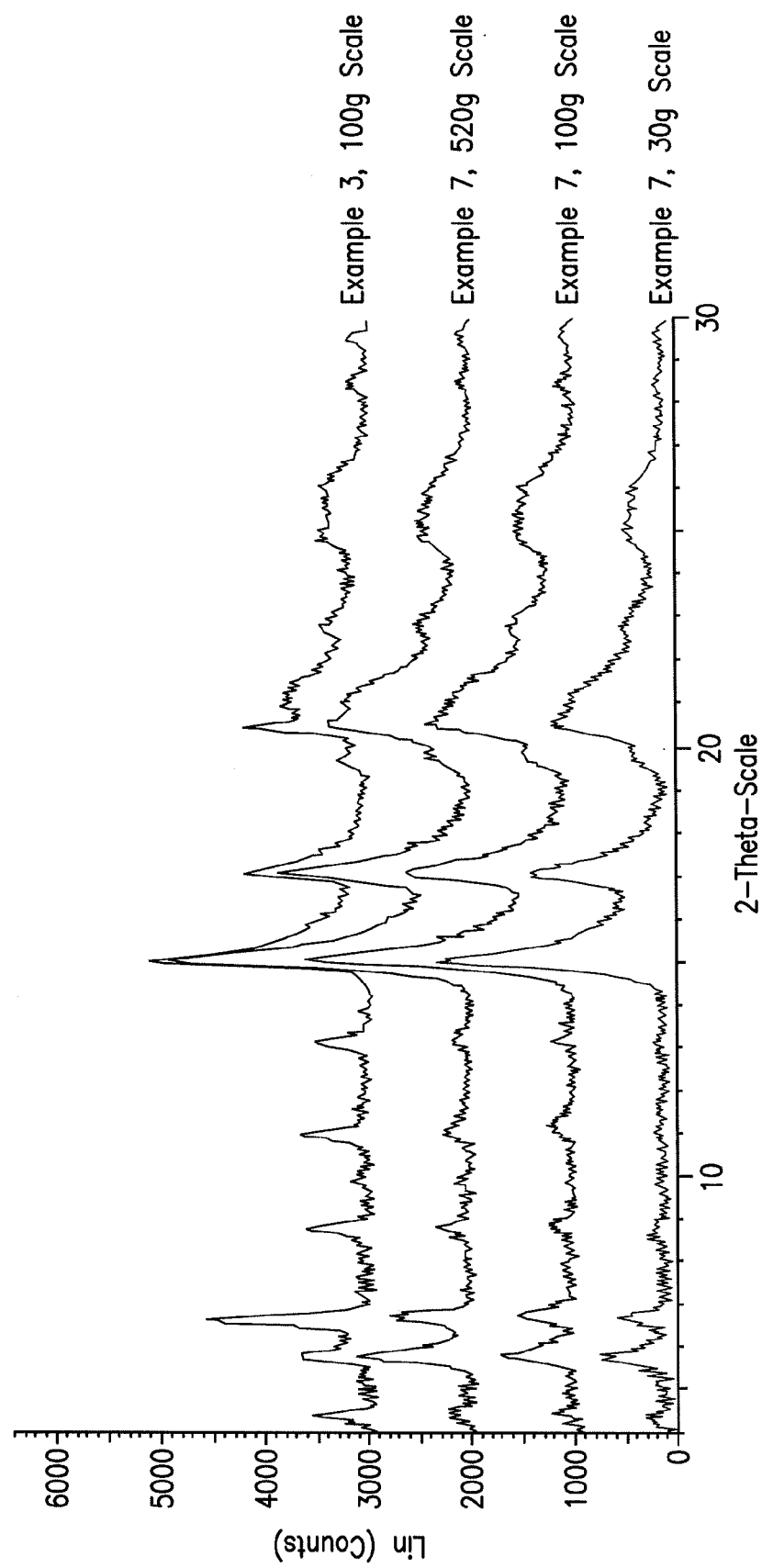
FIG. 16 is a XRPD pattern of solid α-6-mPEG$_6$-O-hydroxycodone phosphate salts prepared according to Examples 3 and 7.

In certain embodiments, the solid form of α-6-mPEG$_6$-O-hydroxycodone phosphate salt has X-ray powder diffraction two theta peak values substantially similar to any one of those of FIG. 16.

In certain embodiments, the solid form of α-6-mPEG$_6$-O-hydroxycodone phosphate salt has X-ray powder diffraction peak values comprising: 2.0±0.2, 15.0±0.2, and 17.0±0.2 degrees two theta, when measured with Cu Kα radiation. In certain embodiments, the solid form of α-6-mPEG$_6$-O-hydroxycodone phosphate salt has X-ray powder diffraction peak values comprising: 2.0±0.2, 5.5±0.2, 15.0±0.2, 17.0±0.2, and 20.5±0.2 degrees two theta, when measured with Cu Kα radiation. In certain embodiments, the solid form of α-6-mPEG$_6$-O-hydroxycodone phosphate salt has X-ray powder diffraction peak values comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has X-ray powder diffraction peak values comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation.

In certain embodiments, the solid form of α-6-mPEG$_6$-O-hydroxycodone phosphate salt has at least one X-ray powder diffraction peak value selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least two X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least three X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least four X-ray powder diffraction peak values selected from the group comprising: 2.0±0.2, 5.5±0.2, 6.5±0.2, 8.5 0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least five X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least six X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least seven X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least eight X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least nine X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least ten X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least eleven X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least twelve X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least thirteen X-ray powder diffraction peak values selected from the group comprising: 2.0±0.2, 5.5±0.2, 6.5±0.2, 8.5±0.2, 11.0±0.2, 13.0±0.2, 15.0±0.2, 17.0±0.2, 19.5±0.2, 20.5±0.2, 25.0±0.2, 28.5±0.2, and 29.5±0.2 degrees two theta, when measured with Cu Kα radiation.

In certain embodiments, the solid form of α-6-mPEG$_6$-O-hydroxycodone phosphate salt has at least one X-ray powder diffraction peak value selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least two X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least three X-ray powder diffraction peak values selected from the group comprising: 2.0±0.2, 4.5±0.2, 5.5±0.2, 6.5±0.2, 8.5 0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least four X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least five X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least six X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least seven X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least eight X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least nine X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least ten X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least eleven X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least twelve X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5± 0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least thirteen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least fourteen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least fifteen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least sixteen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least seventeen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation. In certain embodiments, the solid form of α-6-mPEG$_6$-O-hydroxycodone phosphate salt has at least eighteen X-ray powder diffraction peak values selected from the group comprising: 2.0±0.2, 4.5±0.2, 5.5±0.2, 6.5±0.2, 8.5±0.2, 11.0±0.2, 13.0±0.2, 15.0±0.2, 17.0±0.2, 17.5±0.2, 19.5±0.2, 20.5±0.2, 21.5±0.2, 24.0±0.2, 25.0±0.2, 26.0±0.2, 28.5±0.2, and 29.5±0.2 degrees two theta, when measured with Cu Kα radiation.

In certain embodiments, the solid form of α-6-mPEG$_6$-O-hydroxycodone phosphate salt exhibits a first broad endothermic peak over a range of about 10° C. to about 140° C.; a second endothermic peak at about 160° C. to about 164° C. and a third endothermic peak at about 170° C. to about 173° C. on a differential scanning calorimeter.

In certain embodiments, the solid form of α-6-mPEG$_6$-O-hydroxycodone phosphate salt exhibits an endothermic peak as measured by a differential scanning calorimeter with an onset of about 174° C. to about 179° C. and a peak from about 177° C. to about 181° C. In certain embodiments, the solid form of α-6-mPEG$_6$-O-hydroxycodone phosphate salt exhibits an endothermic peak as measured by a differential scanning calorimeter with an onset of about 175° C. to about 178° C. and a peak from about 178° C. to about 180° C.

In certain embodiments, the solid form of α-6-mPEG$_6$-O-hydroxycodone phosphate salt has a particle size distribution wherein DV[10] is about 3 µm to about 15 µm; DV[50] is about 40 µm to about 60 µm; and DV[90] is about 90 µm to about 120 µm. In certain embodiments, the solid form of α-6-mPEG$_6$-O-hydroxycodone phosphate salt has a particle size distribution wherein DV[10] is about 5 µm to about 13 µm; DV[50] is about 45 µm to about 55 µm; and DV[90] is about 90 µm to about 115 µm. In certain embodiments, the solid form of α-6-mPEG$_6$-O-hydroxycodone phosphate salt has a particle size distribution wherein DV[10] is about 6 µm to about 11 µm; DV[50] is about 45 µm to about 55 µm; and DV[90] is about 90 µm to about 112 µm. In certain embodiments, the solid form of α-6-mPEG$_6$-O-hydroxycodone phosphate salt has a particle size distribution wherein DV[10] is about 7 µm to about 9 µm; DV[50] is about 47 µm to about 53 µm; and DV[90] is about 92 µm to about 109 µm. As is understood by one of skill in the art a DV[Y] value represents that "V" percent of the volume distribution is below the particular size referenced. For example, DV[10] of about 100 µm indicates that 10 percent of the volume distribution is less than about 100 µm.

In certain embodiments, the solid form of α-6-mPEG$_6$-O-hydroxycodone phosphate salt has a particle size distribution wherein DV[10] is about 3 µm to about 15 µm; in certain embodiments, DV[10] is about 5 µm to about 13 µm; in certain embodiments, DV[10] is about 6 µm to about 11 µm; and in certain embodiments, DV[10] is about 7 µm to about 9 µm. In certain embodiments, the solid form of α-6-mPEG$_6$-O-hydroxycodone phosphate salt has a particle size distribution wherein DV[50] is about 40 µm to about 60 µm; in certain embodiments, DV[50] is about 45 µm to about 55 µm; and in certain embodiments, DV[50] is about 47 µm to about 53 µm. In certain embodiments, the solid form of α-6-mPEG$_6$-O-hydroxycodone phosphate salt has a particle size distribution wherein DV[90] is about 90 µm to about 120 µm; in certain embodiments, DV[90] is about 90 µm to about 115 µm; in certain embodiments, DV[90] is about 90 µm to about 112 µm; and in certain embodiments, DV[90] is about 92 µm to about 109 µm.

In certain embodiments, the solid form of α-6-mPEG$_6$-O-hydroxycodone phosphate salt is prepared by dissolving α-6-mPEG$_6$-O-hydroxycodone free base in a mixture of a first solvent and a second solvent; combining the α-6-mPEG$_6$-O-hydroxycodone solution with a solution of phosphoric acid in a third solvent and fourth solvent; combining the α-6-mPEG$_6$-O-hydroxycodone phosphoric acid solution with a fifth solvent and a sixth solvent to form a slurry; and filtering the slurry to yield the α-6-mPEG$_6$-O-hydroxycodone phosphate salt in solid form. In certain embodiments, the first solvent is methanol and the second solvent is tert-butyl methyl ether (tBME, MTBE). In certain embodiments, the first solvent and second solvent are present in a ratio of about 2:1 (volume:volume). In certain embodiments, the volume of the mixture of the first solvent and the second solvent is about two relative volumes. In certain embodiments, the third solvent is methanol and the fourth solvent is tert-butyl methyl ether. In certain embodiments, the third solvent and the fourth solvent are present in a ratio of about 2:1 (volume:volume). In certain embodiments, the volume of the mixture of the third solvent and the fourth solvent is about two relative volumes. In certain embodiments, the volume of the mixture of the third solvent and the fourth solvent is about 1.2 relative volumes. In certain embodiments, the fifth solvent is heptanes and the sixth solvent is tert-butyl methyl ether. In certain embodiments, the fifth solvent and the sixth solvent are present in a ratio of about 4:1 (volume:volume). The mixture of the fifth solvent and the sixth solvent is about 14 relative volumes. In certain embodiments, the α-6-mPEG$_6$-O-hydroxycodone phosphoric acid solution is added to the fifth solvent and sixth solvent over about 1 to about 3 hours to form the slurry. In certain embodiments, prior to filtering, the supernatant solvent mixture is removed and additional heptanes are added to the solid salt form of α-6-mPEG$_6$-O-hydroxycodone phosphate salt at least once. In certain embodiments, the solid salt form of α-6-mPEG$_6$-O-hydroxycodone phosphate salt is washed with about 2 relative volumes of heptanes after filtering.

In certain embodiments, the solid form of α-6-mPEG$_6$-O-hydroxycodone phosphate is prepared by dissolving α-6-mPEG$_6$-O-hydroxycodone free base in about 2 relative volumes of a mixture methanol and tert-butyl methyl ether (2:1 ratio of methanol to tert-butyl methyl ether); combining the α-6-mPEG$_6$-O-hydroxycodone solution with a solution of phosphoric acid in about 1.2 relative volumes of a mixture methanol and tert-butyl methyl ether (2:1 ratio of methanol to tert-butyl methyl ether); combining the α-6-mPEG$_6$-O-hydroxycodone phosphoric acid solution with about 14 relative volumes of a mixture of heptanes and tert-butyl methyl ether (4:1 ratio of heptanes to tert-butyl methyl ether) to form a slurry; optionally removing the supernatant and adding additional heptanes to the slurry; and filtering the slurry to yield the α-6-mPEG$_6$-O-hydroxycodone phosphate salt in solid form. In certain embodiments the α-6-mPEG$_6$-O-hydroxycodone phosphoric acid solution is combined with the mixture of heptanes and tert-butyl methyl ether over about 10 minutes to about 3 hours. In certain embodiments, the slurry can be distilled to remove portions of the methanol solvent. In certain embodiments, the solid salt form of α-6-mPEG$_6$-O-hydroxycodone phosphate salt is washed with about 2 volumes of heptanes after filtering.

In certain embodiments, the solid form of α-6-mPEG$_6$-O-hydroxycodone phosphate is prepared by dissolving α-6-mPEG$_6$-O-hydroxycodone free base in a mixture of tert-butyl methyl ether and a hydrocarbon solvent; adding phosphoric acid to form a slurry; stirring the slurry, and filtering to recover the solid α-6-mPEG$_6$-O-hydroxycodone phosphate salt. In certain embodiments, the hydrocarbon solvent is a hydrocarbon having from 3 to 10 carbon atoms. In certain embodiments, the hydrocarbon solvent is heptane. In certain embodiments, the hydrocarbon solvent is a mixture of isomers of heptane (i.e. heptanes). In certain embodiments, the solid form of α-6-mPEG$_6$-O-hydroxycodone phosphate is prepared by dissolving α-6-mPEG$_6$-O-hydroxycodone free base in a mixture of tert-butyl methyl ether and heptanes; adding phosphoric acid to form a slurry; stirring the slurry, and filtering to recover the solid α-6-mPEG$_6$-O-hydroxycodone phosphate salt. In certain embodiments, the phosphoric acid is added over a time of about 30 minutes to about 3 hours. In certain embodiments, the phosphoric acid is added over about 1 hour. In certain embodiments, the phosphoric acid is added at about ten minute intervals over the course of about 30 minutes to about 3 hours. In certain embodiments, the phosphoric acid is added at about ten minute intervals over the course of about 1 hour. In certain embodiments, the solid α-6-mPEG$_6$-O-hydroxycodone phosphate salt is washed with tert-butyl methyl ether. In certain embodiments, the solid α-6-mPEG$_6$-O-hydroxycodone phosphate salt is washed with heptanes. In certain embodiments, the amount of α-6-mPEG$_6$-O-hydroxycodone free base is "X" kilograms. In certain embodiments, the volume of tert-butyl methyl ether is 5*"X" liters and the volume of heptanes is "X' liters. In certain embodiments, the volume to volume ratio of tert-butyl methyl ether to heptanes is about 5:1. In certain embodiments the amount of phosphoric acid is about 0.80 molar equivalents to about 1.20 molar equivalents. In certain embodiments, the amount of phosphoric acid is about 0.90 to about 1.10 molar equivalents. In certain embodiments, the amount of phosphoric acid is about 1.0 molar equivalents. In certain embodiments, the amount of phosphoric acid is about 1.01 molar equivalents. In certain embodiments, the amount of phosphoric acid (kg) is equal to ("n"*"X") where n is about [(16 to 17)/"assay value of phosphoric acid"]. In certain embodiments, the amount of phosphoric acid (kg) is equal to "n"*"X" where n is about 16.6/"assay value of phosphoric acid". In certain embodiments, the amount of phosphoric acid (kg) is equal to "n"*"X" where n is about 16.614/"assay value of phosphoric acid". The "assay value of phosphoric acid" refers to the value (w/w %) reported by the manufacturer's analysis. In certain embodiments, the phosphoric acid is an aqueous phosphoric acid solution. In certain embodiments, the aqueous phosphoric acid solution is about an 85 percent solution in water. In certain embodiments, after the phosphoric acid has been added, the solution is allowed to stir for about 1 to about 4 hours. In certain embodiments, after the phosphoric acid has been added, the solution is allowed to stir for about 2 hours. In certain embodiments, the solution of α-6-mPEG$_6$-O-hydroxycodone free base is maintained at a temperature of about 15° C. In certain embodiments, the solution of α-6-mPEG$_6$-O-hydroxycodone is maintained at a temperature of about 15° C. while the phosphoric acid is being added. In certain embodiments, the solution of α-6-mPEG$_6$-O-hydroxycodone is maintained at a temperature of about 15° C. throughout the addition of phosphoric acid. In certain embodiments, the reaction mixture contains water. In certain embodiments, the amount of water is about 0.4-0.8 wt %.

In certain embodiments, the solid α-6-mPEG$_6$-O-hydroxycodone D-tartrate salt form is a monotartrate salt. That is, the tartrate anion and α-mPEG$_6$-O-hydroxycodone cation are present in about a 1:1 ratio.

Figure 7:
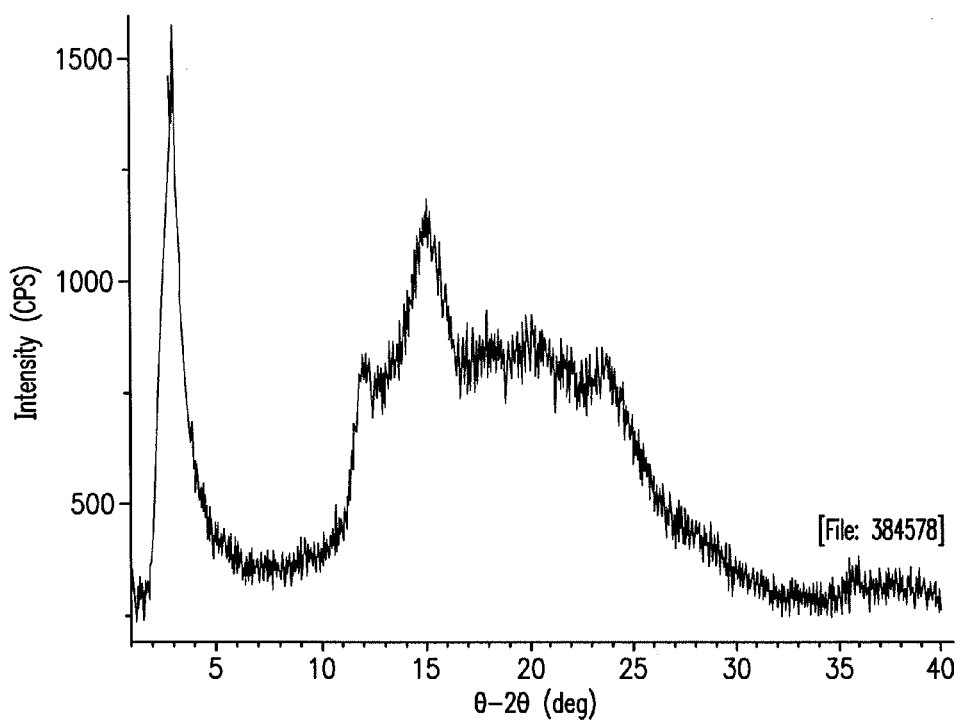
FIG. 7 is an XRPD pattern of the solid α-6-mPEG$_6$-O-hydroxycodone D-tartaric acid salt as prepared according to Example 1.
Figure 12:
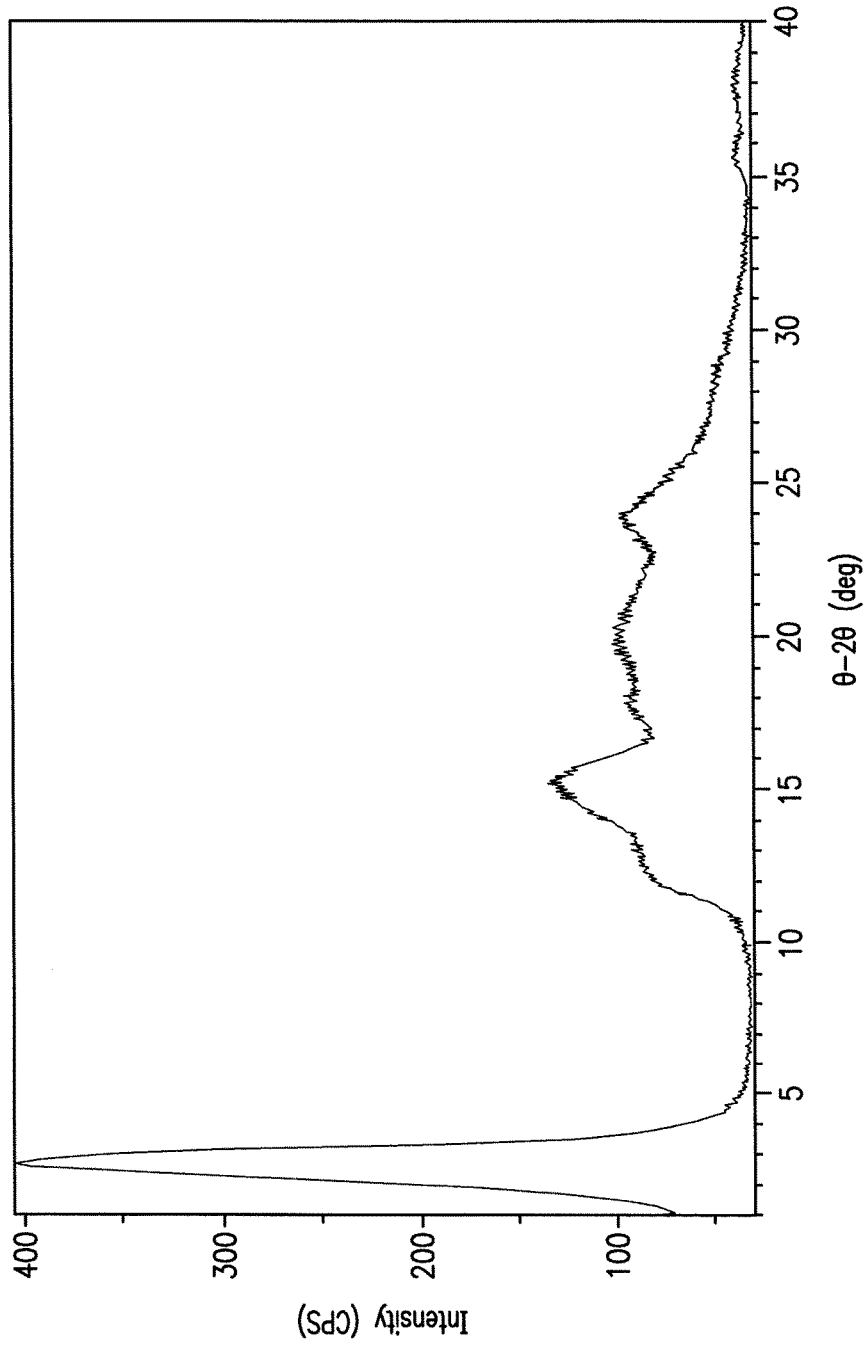
FIG. 12 is a XRPD pattern of the solid α-6-mPEG$_6$-O-hydroxycodone D-tartaric acid salt as prepared according to Example 4.

In certain embodiments, the solid form of α-6-mPEG$_6$-O-hydroxycodone D-tartrate salt has X-ray powder diffraction two theta peak values substantially similar to those of FIG. 7 and/or FIG. 12. In certain embodiments, the solid form of α-6-mPEG$_6$-O-hydroxycodone D-tartrate salt has X-ray powder diffraction peak values comprising: 2.5±0.2 and 15.0±0.2 degrees two theta, when measured with Cu Kα radiation. In certain embodiments, the solid form of α-6-mPEG$_6$-O-hydroxycodone D-tartrate salt has X-ray powder diffraction peak values comprising: 2.5±0.2, 15.0±0.2, 20.0±0.2, and 23.5±0.2 degrees two theta, when measured with Cu Kα radiation.

In certain embodiments, the solid form of α-6-mPEG$_6$-O-hydroxycodone D-tartrate salt exhibits a first broad endothermic peak over a range of about 40° C. to about 107° C. and a second endothermic peak at about 126° C. on a differential scanning calorimeter.

In certain embodiments, the solid form of α-6-mPEG$_6$-O-hydroxycodone D-tartrate is prepared by dissolving α-6-mPEG$_6$-O-hydroxycodone free base in a first solvent; combining the α-6-mPEG$_6$-O-hydroxycodone solution with a solution of D-tartaric acid in a second solvent; adding a third solvent to the mixture of the α-6-mPEG$_6$-O-hydroxycodone solution and the D-tartaric acid solution to form a slurry; and filtering the slurry to yield the α-6-mPEG$_6$-O-hydroxycodone D-tartrate salt in solid form. In certain embodiments, the first solvent is tetrahydrofuran. In certain embodiments, the volume of the first solvent is about 2 relative volumes. In certain embodiments, the second solvent is tetrahydrofuran. In certain embodiments, the volume of the second solvent is about 2 relative volumes. In certain embodiments, the third solvent is heptanes. In certain embodiments, the volume of the third solvent is about 6 relative volumes. In certain embodiments, the third solvent is added to the mixture of the α-6-mPEG$_6$-O-hydroxycodone and D-tartaric acid solution over about 30 minutes In certain embodiments, the solid form of α-6-mPEG$_6$-O-hydroxycodone D-tartrate is prepared by dissolving α-6-mPEG$_6$-O-hydroxycodone free base in about 2 relative volumes of tetrahydrofuran; combining the α-6-mPEG$_6$-O-hydroxycodone solution with a solution of D-tartaric acid in about 2 relative volumes of tetrahydrofuran; adding about 6 equivalents of heptanes to the α-6-mPEG$_6$-O-hydroxycodone D-tartaric acid solution to form a slurry; and filtering the slurry to yield the α-6-mPEG$_6$-O-hydroxycodone D-tartrate salt in solid form. In certain embodiments, the heptanes are added over about 30 minutes. In certain embodiments, the solid α-6-mPEG$_6$-O-hydroxycodone D-tartrate salt is washed with about 2 volumes of heptanes after filtering.

It will be recognized that in their solid forms, α-6-mPEG$_6$-O-hydroxycodone salts provided herein (e.g. phosphate salts) can exhibit desirable characteristics for the preparation, processing and/or storage of a pharmaceutical composition or drug product. As such, in certain embodiments, pharmaceutical compositions are provided that comprise a solid α-6-mPEG$_6$-O-hydroxycodone salt and a pharmaceutically acceptable excipient and/or carrier. The choice of excipient, to a large extent, depends on factors, such as the particular mode of administration, the effect of the excipient on the solubility and stability of the active ingredient, and the nature of the dosage form.

Exemplary solids include granules, pellets, beads, powders, which can be administered "as-is" or formulated into one or more of the following for administration to a patient: a tablet; a capsule; a caplet; a suppository; and a troche. In certain embodiments, the composition will be in a unit dosage form to thereby provide a unit dosage suitable for single administration of a dosage of α-6-mPEG$_6$-O-hydroxycodone in the unit dosage form. Suitable pharmaceutical compositions and dosage forms may be prepared using conventional methods known to those in the field of pharmaceutical formulation and described in the pertinent texts and literature, e.g. *Remington: The Science and Practice of Pharmacy*, 21$^{st}$ edition (Lippincott Williams & Wilkins, Philadelphia, Pa. 2005).

In certain embodiments, the pharmaceutical composition is in an oral dosage form, for example, tablets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques may be used when preparing tablets or caplets containing the α-6-mPEG$_6$-O-hydroxycodone salt forms described herein. In addition to the α-6-mPEG$_6$-O-hydroxycodone salt, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., *acacia* sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

In certain embodiments, the tablet can be in the form of a uniform tablet. In uniform tablets the formulation used in preparing the tablet is a substantially homogeneous mixture of one or more active agents and one or more pharmaceutical excipients (e.g., diluents). The formulation is then used to make tablets using a suitable tableting process to thereby result in a tablet that is substantially homogenous throughout the tablet.

Capsules are also suitable oral dosage forms, in which case the composition may be encapsulated in the form of a liquid, semi-solid or solid (including particulates such as granules, beads, powders or pellets). Suitable capsules may be either hard or soft, and are generally made of gelatin, starch, or a cellulosic material. In certain embodiments the capsules are gelatin. Two-piece hard gelatin capsules are preferably sealed, such as with gelatin bands or the like. See, for example, *Remington: The Science and Practice of Pharmacy*, supra, which describes materials and methods for preparing encapsulated pharmaceuticals.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical compositions encompass all types of formulations. The amount of the active agent (i.e., solid α-6-mPEG$_6$-O-hydroxycodone salt form) in the composition will vary depending on a number of factors, but will optimally be a therapeutically effective dose the active agent when the composition is stored in a unit dose form. A therapeutically effective dose for the active agent can be determined experimentally by repeated administration of increasing amounts of the active agent in order to determine which amount produces a clinically desired endpoint. In certain embodiments, the amount of a solid salt form α-6-mPEG$_6$-O-hydroxycodone in the composition is within the range of about 5 mg to about 1000 mg. In certain embodiments, the amount of a solid salt form α-6-mPEG$_6$-O-hydroxycodone in the composition is within the range of about 50 mg to about 750 mg. In certain embodiments, the amount of a solid salt form α-6-mPEG$_6$-O-hydroxycodone in the composition is within the range of about 100 mg to about 500 mg. In certain embodiments, the amount of a solid salt form α-6-mPEG$_6$-O-hydroxycodone in the composition is about 20 mg; about 40 mg, about 50 mg; about 80 mg; about 100 mg; about 125 mg; about 150 mg; about 200 mg; about 250 mg; about 300 mg; about 350 mg; about 400 mg; about 450 mg; or about 500 mg.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters of the composition, and then determining the range at which optimal performance is attained with no significant adverse effects. Exemplary excipients are described, for instance, in *Handbook of Pharmaceutical Excipients, 5$^{th}$* Edition (Rowe et al., editors; American Pharmaceutical Association Publications, Washington D.C., 2005).

In certain embodiments, a composition may be formed using the free base form of α-6-mPEG$_6$-O-hydroxycodone. In certain embodiments, the composition is a tablet. The free base form of α-6-mPEG$_6$-O-hydroxycodone exists as a viscous liquid at ambient storage conditions. Generally, such materials provide challenges for solid formulations. The free base form of α-6-mPEG$_6$-O-hydroxycodone may be converted to a free flowing solid by submitting α-6-mPEG$_6$-O-hydroxycodone and certain tablet components to a high speed granulator and mixing. In certain embodiments, the α-6-mPEG$_6$-O-hydroxycodone free base is added to a suitable solvent (e.g. water, citric acid solution) to provide a flowing liquid; all excipients are charged into a bowl in a high speed granulator; the solution containing α-6-mPEG$_6$-O-hydroxycodone is added to the excipient mixture and mixed; the wet granules are dried; extra granule materials are added and the mixture is further mixed, and the mixture is pressed into tablets. In certain embodiments, an aqueous solution of a binder, such as polyvinyl pyrolidine (PVP), hydroxypropyl methyl cellulose or hypromellose (HPMC), hydroxypropyl cellulose (HPC), etc., is added to the mixture in the high speed granulator and mixed. In certain embodiments a film coating is added to the final tablets. In certain embodiments, the maximum drug loading for such tablets is about 14 percent. In certain embodiments, the drug loading for the tablet is less than about 20 percent; in certain embodiments the drug loading for the tablet is less than about 18 percent; in certain embodiments the drug loading for the tablet is less than about 16 percent; in certain embodiments the drug loading for the tablet is less than about 14 percent; in certain embodiments the drug loading for the tablet is less than about 12 percent; and in certain embodiments the drug loading for the tablet is less than about 10 percent.

Example 5 provides exemplary tablets formed with the α-6-mPEG$_6$-O-hydroxycodone free base.

The formulations prepared using the free base of α-6-mPEG$_6$-O-hydroxycodone are unique in that they result in the formation of free flowing granules that have adequate compressibility and can be formulated, for example, as hard gelatin capsules or tablets. The granules are formed from a viscous liquid (α-6-mPEG$_6$-O-hydroxycodone freebase) without the use of adsorbants, antiadherants, and/or detackifying agents, which may often be employed when working with a highly viscous substance. Further, the use of an acid, for example, citric acid, resulted in better flow and compressibility when compared to granules that did not include an acid, for example, citric acid. As such, the granules formed demonstrate a means for producing free flowing granules from a viscous liquid. Tablets formed from those granules exhibited adequate hardness and friability along with rapid disintegration. Tables 4-6.

In certain embodiments, a composition may be formed from the solid α-6-mPEG$_6$-O-hydroxycodone phosphate salt form disclosed herein. In certain embodiments, the composition is a tablet. In certain embodiments, the solid α-6-mPEG$_6$-O-hydroxycodone phosphate salt form is converted to a free flowing solid by submitting the solid α-6-mPEG$_6$-O-hydroxycodone phosphate salt and certain tablet components to a high speed granulator and mixing. In certain embodiments, the tablet comprises intra granular components. In certain embodiments, the tablet comprises intra granular and extra granular components. In certain embodiments, the solid α-6-mPEG$_6$-O-hydroxycodone phosphate salt form and solid excipients are added to a bowl in a high speed granulator and mixed, a solution of a binder, such as polyvinyl pyrolidine (PVP), hydroxypropyl methyl cellulose (HPMC), hydroxypropyl cellulose (HPC), etc. and water is added while mixing, the wet mixture is dried to form dry granules; extra granular materials are added and the mixture is further mixed; and the mixture is pressed into tablets. In certain embodiments, a film coating is added to the final tablets. In certain embodiments, the tablet has a drug loading of greater than about 5 percent; in certain embodiments greater than about 10 percent; in certain embodiments greater than about 15 percent; in certain embodiments greater than about 20 percent; in certain embodiments greater than about 25 percent; in certain embodiments greater than about 30 percent; in certain embodiments greater than about 35 percent; in certain embodiments greater than about 40 percent; in certain embodiments greater than about 45 percent. In certain embodiments, the drug loading is in the range of about 15 percent to about 50 percent. In certain embodiments, the drug loading is in the range of about 20 percent to about 45 percent. In certain embodiments, the drug loading is in the range of about 25 percent to about 40 percent. In certain embodiments, the drug loading is in the range of about 30 percent to about 40 percent. In certain embodiments, the drug loading is in the range of about 33 percent to about 37 percent. In certain embodiments, the drug loading is about 35 percent. In certain embodiments, the drug loading is about 30 percent. In certain embodiments, the drug loading is about 25 percent. In certain embodiments, the drug loading is about 26 percent. In certain embodiments, the drug loading is about 27 percent. In certain embodiments, the drug loading is about 28 percent. In certain embodiments, the drug loading is about 29 percent. In certain embodiments, the drug loading is about 31 percent. In certain embodiments, the drug loading is about 32 percent. In certain embodiments, the drug loading is about 33 percent. In certain embodiments, the drug loading is about 34 percent.

In certain embodiments of a tablet described herein, the tablet has a friability of less than about 1.0 percent. In certain embodiments, the tablet has a friability of less than about 0.5 percent. In certain embodiments, the tablet has a friability of less than about 0.1 percent. In certain embodiments the tablet has a friability of less than about 0.05 percent.

In certain embodiments, the tablet comprises only intragranular components. In certain embodiments, the solid α-6-mPEG$_6$-O-hydroxycodone phosphate salt form and solid excipients are added to a bowl and blended (e.g. a V-blender), and the mixture is pressed into tablets. In certain embodiments, one of more excipient is selected from the group comprising dibasic calcium phosphate, microcrystalline cellulose, croscarmellose sodium, colloidal silicon dioxide, and magnesium stearate. Additional excipients may also be included. In certain embodiments, the excipients comprise the group comprising dibasic calcium phosphate, microcrystalline cellulose, croscarmellose sodium, colloidal silicon dioxide, and magnesium stearate. In certain embodiments, the a film coating is added to the tablets. In certain embodiments, the tablet has a drug loading of greater than about 5 percent; in certain embodiments greater than about 10 percent; in certain embodiments greater than about 15 percent; in certain embodiments greater than about 20 percent; in certain embodiments greater than about 25 percent; in certain embodiments greater than about 30 percent; in certain embodiments greater than about 35 percent; in certain embodiments greater than about 40 percent; in certain embodiments greater than about 45 percent. In certain embodiments, the drug loading is in the range of about 15 percent to about 50 percent. In certain embodiments, the drug loading is in the range of about 20 percent to about 45 percent. In certain embodiments, the drug loading is in the range of about 25 percent to about 40 percent. In certain embodiments, the drug loading is in the range of about 30 percent to about 40 percent. In certain embodiments, the drug loading is in the range of about 33 percent to about 37 percent. In certain embodiments, the drug loading is about 35 percent. In certain embodiments, the drug loading is about 30 percent. In certain embodiments, the drug loading is about 25 percent. In certain embodiments, the drug loading is about 26 percent. In certain embodiments, the drug loading is about 27 percent. In certain embodiments, the drug loading is about 28 percent. In certain embodiments, the drug loading is about 29 percent. In certain embodiments, the drug loading is about 31 percent. In certain embodiments, the drug loading is about 32 percent. In certain embodiments, the drug loading is about 33 percent. In certain embodiments, the drug loading is about 34 percent. In certain embodiments of a tablet described herein, the tablet has a friability of less than about 1.0 percent. In certain embodiments, the tablet has a friability of less than about 0.5 percent. In certain embodiments, the tablet has a friability of less than about 0.1 percent. In certain embodiments the tablet has a friability of less than about 0.05 percent. In certain embodiments the tablet has a friability of less than about 0.02 percent.

Examples 6, 8, and 9 provide exemplary tablets formed with the solid α-6-mPEG$_6$-O-hydroxycodone phosphate salt.

Tablets and compositions of the solid form of the α-6-mPEG$_6$-O-hydroxycodone tartrate salt may be formed according to the methods known to those of skill in the art, as well as those disclosed above or the Examples provided below.

Generally, however, the excipient(s) will be present in the composition in an amount of about 1% to about 99% by weight, in certain embodiments from about 2%-98% by weight, in certain embodiments from about 5-95% by weight of the excipient, and in certain embodiments less than 30% by weight.

In certain embodiments, provided herein is a method for administering the solid salt form of α-6-mPEG$_6$-O-hydroxycodone as described herein. In certain embodiments, the method comprises administering a composition as provided herein to a patient suffering from a condition that is responsive to treatment with an opioid agonist. In certain embodiments, the method comprises administering a unit dosage form described herein. The method of administering may be used to treat any condition that can be remedied or prevented by administration of the opioid agonist (e.g., moderate to severe pain). As the cause of the pain is not necessarily critical to the methods disclosed herein, the methods include the treatment of pain arising from various sources, injuries, and disease states. Those of ordinary skill in the art appreciate which conditions an opioid agonist can effectively treat, for example, nociceptive pain. In certain embodiments, the condition includes neuropathic pain. The actual dose administrated will vary depending on the age, weight, and general condition of the subject as well as the severity of the condition being treated, the judgment of the health care professional, and the active ingredient being administered. Therapeutically effective amounts are known to those of skill in the art and for described in the pertinent reference texts and literature. Generally, a therapeutically effective amount will range from about 0.01 mg to about 750 mg. In certain embodiments the dose ranges from about 10 mg to about 750 mg. In certain embodiments the dose ranges from about 50 mg to about 500 mg. In certain embodiments, the dose ranges from about 5 mg to about 500. In certain embodiments the dose ranges from about 100 mg to about 500 mg. In certain embodiments the dose ranges from about 150 mg to about 450 mg. In certain embodiments, the dose is selected from the group comprising about 10 mg; about 20 mg; about 40 mg; about 50 mg; about 80 mg; about 100 mg; about 125; about 150; about 160 mg; about 200 mg; about 250 mg; about 300 mg; about 320 mg; about 350 mg; about 400 mg; about 450 mg; and about 500 mg.

The solid salt form of α-6-mPEG$_6$-O-hydroxycodone, pharmaceutical composition comprising the solid salt form of α-6-mPEG$_6$-O-hydroxycodone, and/or dosage form (e.g., a unit dosage form) described herein, can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. In certain embodiments, the solid salt form of α-6-mPEG$_6$-O-hydroxycodone is administered as necessary over a 24 hour period to manage moderate to severe pain. Management of moderate to severe pain includes treating and/or preventing pain. In certain embodiments, the solid salt form of α-6-mPEG$_6$-O-hydroxycodone is administered as necessary over a 24 hour period to treat and/or prevent moderate to severe pain. In certain embodiments, the solid salt form of α-6-mPEG$_6$-O-hydroxycodone is administered as necessary over a 24 hour period to treat moderate to severe pain. In certain embodiments, the solid salt form of α-6-mPEG$_6$-O-hydroxycodone is administered as necessary over a 24 hour period to prevent moderate to severe pain. As is understood by one of skill in the art, administration of the solid salt form of α-6-mPEG$_6$-O-hydroxycodone may also include administration of a pharmaceutical composition comprising the solid salt form of α-6-mPEG$_6$-O-hydroxycodone, and/or dosage form composition comprising the solid salt form of α-6-mPEG$_6$-O-hydroxycodone (e.g., a unit dosage form).

It is to be understood that while the invention has been described in conjunction with certain embodiments thereof, that the foregoing description as well as the experimental that follow are intended to illustrate and not limit the scope of the invention.

EXAMPLES

Reagents and solvents used below can be obtained from commercial sources such as Aldrich Chemical Co. (Milwaukee, Wis., U.S.A.). Routine chemical and physiological analyses were conducted following standard operating procedures known to those skilled in the art. For example, certain analyses were performed as described in the following paragraphs.

XRPD.

In certain instances, XRPD patterns were collected using an Inel XRF-3000 diffractometer equipped with a CPS (Curved Position Sensitive) detector with a °2θ (degree two-theta) range of 120°. Real time data were collected using Cu-Kα radiation at a resolution of 0.03 °2θ. The tube voltage and amperage were set to 40 kV and 30 mA, respectively. The monochromator slit was set at 5 mm by 160 μm. The pattern is displayed from 2.5-40 °2θ. Samples were packed into thin-walled glass capillaries for analysis. Each capillary was mounted onto a goniometer head that is motorized to permit spinning of the capillary during data acquisition. Samples were analyzed for 300 seconds. Instrument calibration was performed using a silicon reference standard.

In other instances, XRPD patterns were collected on a PANalytical X'Pert Prio diffractometer. The samples were analyzed using Cu Kα radiation produced using an Optix long fine-focus source. An elliptically graded multilayer mirror was used to focus the Cu-Kα X-rays of the source through the specimen and onto the detector. The specimen was sandwiched between 3-micron thick films, analyzed in transmission geometry, and rotated to optimize orientation statistics. A beamstop was used to minimize the background generated by air scattering. Helium and anti-scatter extension were used. Soller slits were used for the incident and diffracted beams to minimize axial divergence. The diffraction patterns were collected using a scanning position-sensitive detector (X'Celerator) located 240 mm from the specimen. Prior to the analysis a silicon specimen (NIST standard reference material 640c) was analyzed to verify the position of the silicon 111 peak.

Thermogravimetric Analysis (TGA).

TGA was performed using a TA Instruments Q50001R thermogravimetric analyzer. Each sample was placed in an aluminum sample pan, inserted into the TG furnace, and accurately weighed. The furnace was heated from ambient temperature under nitrogen at a rate of 10° C./min, up to a final temperature of 350° C. Nickel and Alumel™ were used as the calibration Differential Scanning Calorimetry (DSC).

DSC analysis was performed using a T A Instruments differential scanning calorimeter Q2000. Each sample was placed into an aluminum DSC pan, and its weight accurately recorded. Hermetically sealed laser pin hole or lid covered and crimped pan was used. The sample cell was equilibrated at −30° C. and heated under a nitrogen purge at a rate of 10° C./min, up to final temperatures of 200° C. or 250° C. Indium metal was used as the calibration standard. Reported temperatures are at the transition maxima or as a range.

Moisture Sorption.

Moisture sorption/desorption data were collected on a VTI SGA-1 00 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Nuclear Magnetic Resonance Spectroscopy (NMR).

Solution $^1$H-NMR spectra were acquired. Details regarding the scan parameters are included on the relevant figures.

Hotstage Microscopy.

Hot stage microscopy was performed using a Linkam hot stage model FTIR 600 equipped with a TMS93 controller and mounted under a Leica DM LP microscope. The sample was observed using a 20× objective with crossed polarizers and a first order red compensator in place during heating of the stage. Images were captured using a SPOT Insight™ color digital camera with SPOT Software v. 4.5.9. The hot stage was calibrated using USP melting point standards.

Elemental Analysis.

Elemental analysis for carbon, hydrogen, nitrogen and phosphorus was performed by Exova, of Santa Fe Springs, Calif.

Example 1

Preparation of Phosphate Salt of α-6-mPEG$_6$-O-Hydroxycodone

The free base, α-6-mPEG$_6$-O-hydroxycodone, may be prepared using methods known in the art, for example, as described in U.S. Pat. No. 8,173,666. In the examples that follow, mixtures of α-6-mPEG$_6$-O-hydroxycodone and solvent were prepared and assessed under various conditions for solid formation. Potential counter ions of a number of acids were tested to assess whether they might form a solid salt with α-6-mPEG$_6$-O-hydroxycodone. Table 1 below summarizes the acid counter ions that were tested.

TABLE 1

| | | |
|---|---|---|
| Acetic acid | L-Lactic acid | Phosphoric acid, monolithium salt |
| D-Aspartic | Maleic acid | Phosphoric acid, monosodium salt |
| L-Aspartic | R-Mandelic acid | Succinic acid |
| Benzoic acid | S-Mandelic acid | Sulfuric acid |
| Citric acid | D-Malic acid | D-Tartaric acid |
| R-Camphor-10-sulfonic acid | L-Malic acid | L-Tartaric acid |
| S-Camphor-10-sulfonic acid | Methanesulfonic acid | 4-Toluenesulfonic acid |
| Ethane-1,2-disulfonic acid | Orotic acid | Toluic |
| Fumaric acid | Oxalic acid | Trifluoroacteic acid |
| Hydrochloric acid | Phosphoric acid | |

Based on the initial experiments and the properties of the solids generated, phosphoric acid and D-tartaric acid were identified as potentially viable salt forms. Those salts were prepared according to following methods.

Figure 2:
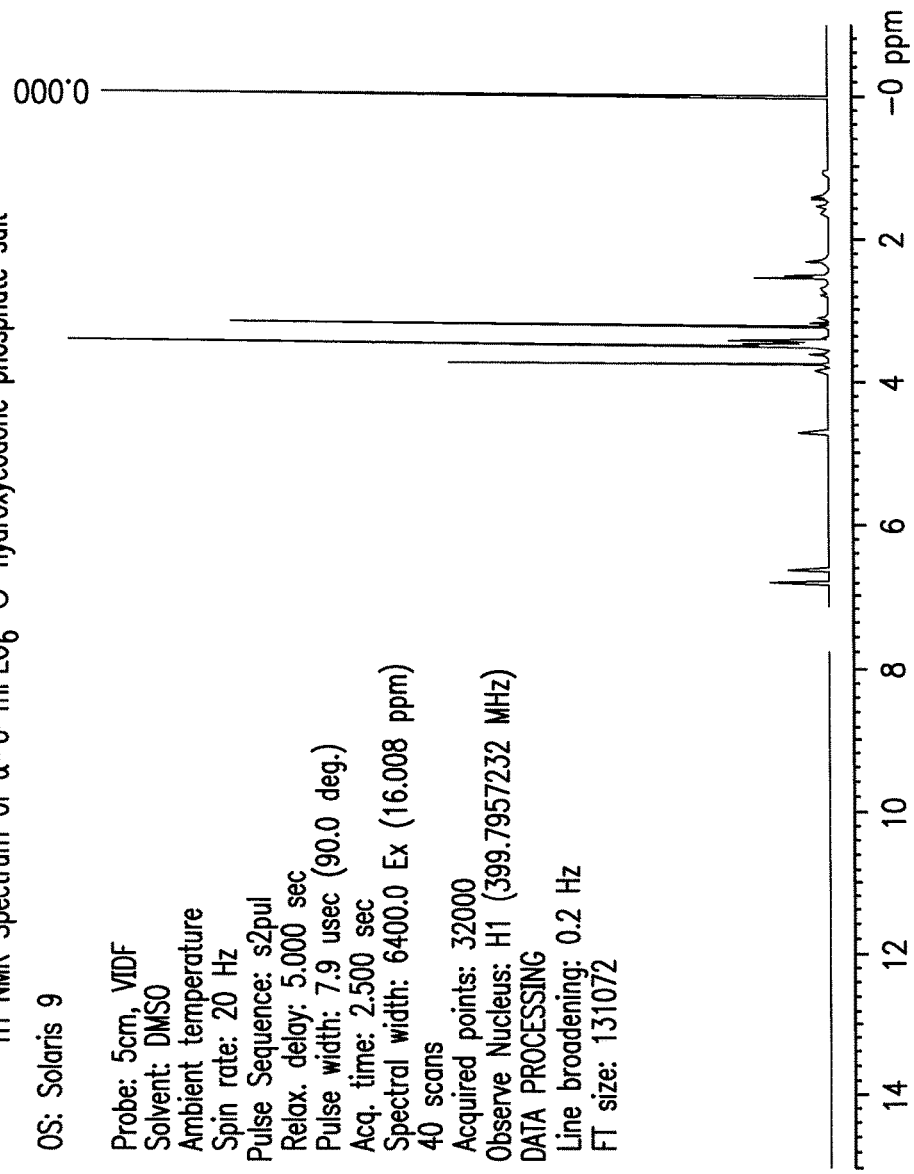
FIG. 2 is a 1H NMR of the solid α-6-mPEG$_6$-O-hydroxycodone phosphate salt prepared according to Example 1, taken in DMSO.
Figure 3:
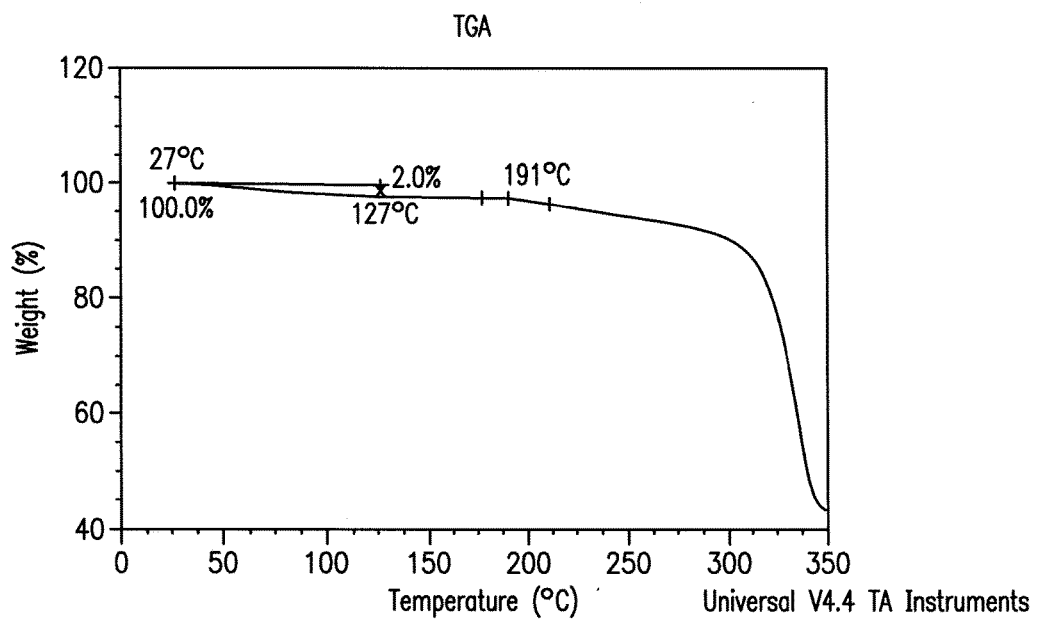
FIG. 3 is a thermogravimetirical analysis (TGA) of the solid α-6-mPEG$_6$-O-hydroxycodone phosphate salt prepared according to Example 1.
Figure 4:
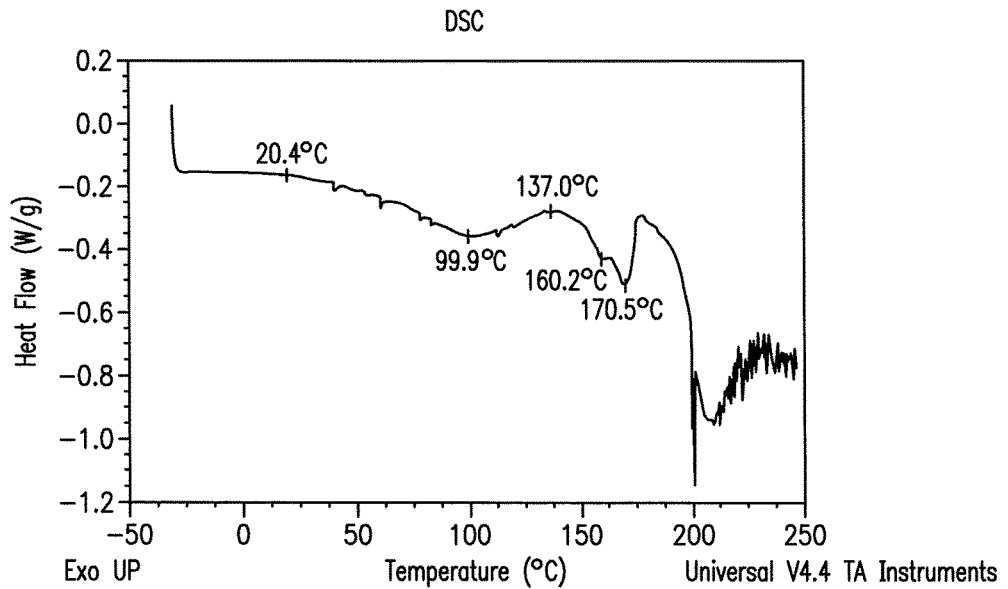
FIG. 4 is a differential scanning calorimetry (DSC) analysis of the solid α-6-mPEG$_6$-O-hydroxycodone phosphate salt prepared according to Example 1.

Phosphoric Acid Salt:

To 500 mg of α-6-mPEG$_6$-O-hydroxycodone dissolved in 2 ml THF was added 54 μL of a 14.6M solution of phosphoric acid. To the solution was added 2 ml of heptane and a white precipitate formed. The mixture stirred for about 3 hours. An additional 2 ml of heptane was added and a white precipitate formed. The mixture was stirred for 3 days and the precipitate was isolate by vacuum filtration, yielding the monophosphate salt (74% yield). FIG. 1 is an XRPD pattern of the phosphoric acid salt. FIG. 2 is a $^1$H NMR of the phosphoric acid salt taken in DMSO. FIG. 3 is a thermogravimetirical analysis (TGA) of the phosphoric acid salt. FIG. 4 is a differential scanning calorimetry (DSC) analysis of the phosphoric acid salt. Elemental analysis confirmed the presence of phosphoric acid in a 1:1 ratio with the free base, indicating a monophosphate salt.

Figure 5:
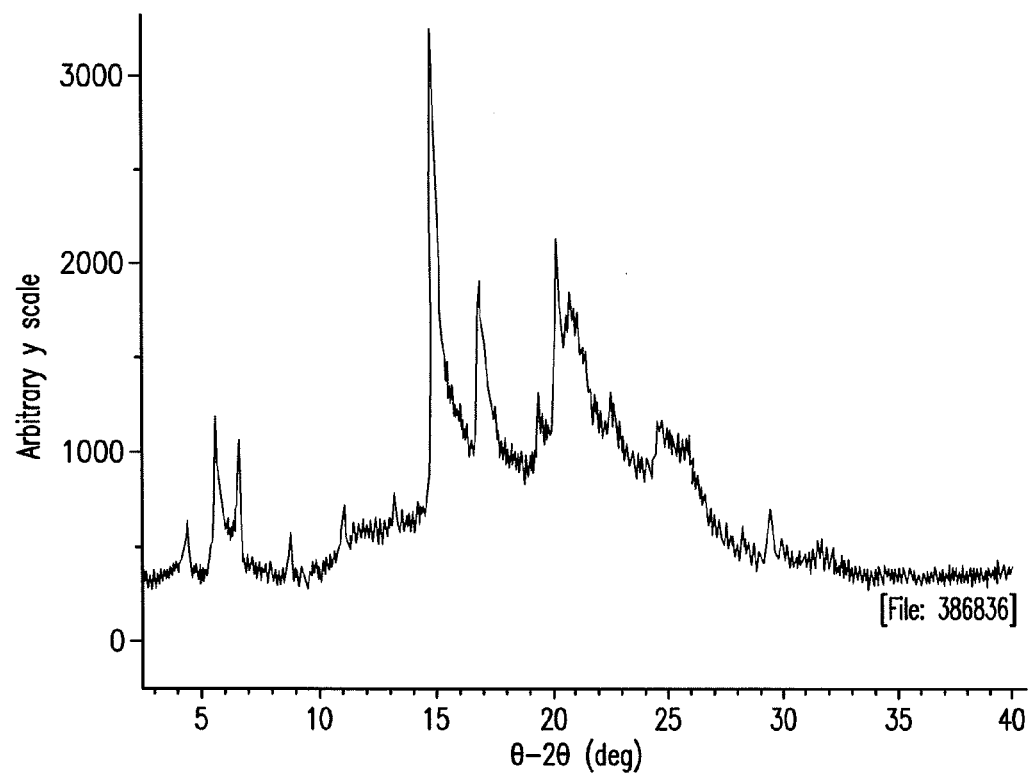
FIG. 5 is an XRPD pattern for the solid α-6-mPEG$_6$-O-hydroxycodone phosphate salt (~900 mg scale) prepared according to Example 1.
Figure 6:
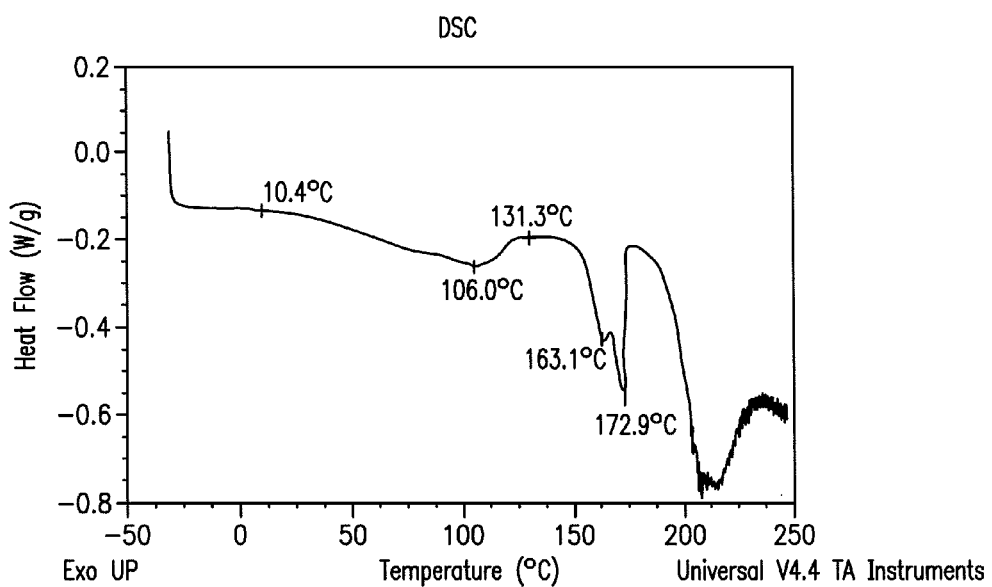
FIG. 6 is a differential scanning calorimetry (DSC) analysis of the solid α-6-mPEG$_6$-O-hydroxycodone phosphate salt (~900 mg scale) prepared according to Example 1

The phosphoric acid salt of α-6-mPEG$_6$-O-hydroxycodone was also formed on a larger scale by dissolving 902.9 mg of α-6-mPEG$_6$-O-hydroxycodone in 3.6 mL of tetrahydrofuran, resulting in a clear solution following brief sonication. 104 μl, of a ~14.6 M phosphoric acid solution was added, upon which white precipitation was observed. 3.6 mL of heptane was added and the sample was stirred for ~6.5 hours. An additional 3.6 mL of heptane was added and the sample was allowed to stir at room temperature for approximately one day. The resulting solids were isolated by vacuum filtration using a 0.2 micron nylon filter. The filtration process was observed to be slow. The solids were dried in a vacuum oven at ambient for approximately one day. The calculated yield assuming a 1:1 phosphate salt formed was approximately 82%. FIG. 5 is an XRPD pattern of the phosphoric acid salt. FIG. 6 is a differential scanning calorimetry (DSC) analysis of the phosphoric acid salt.

Figure 8:
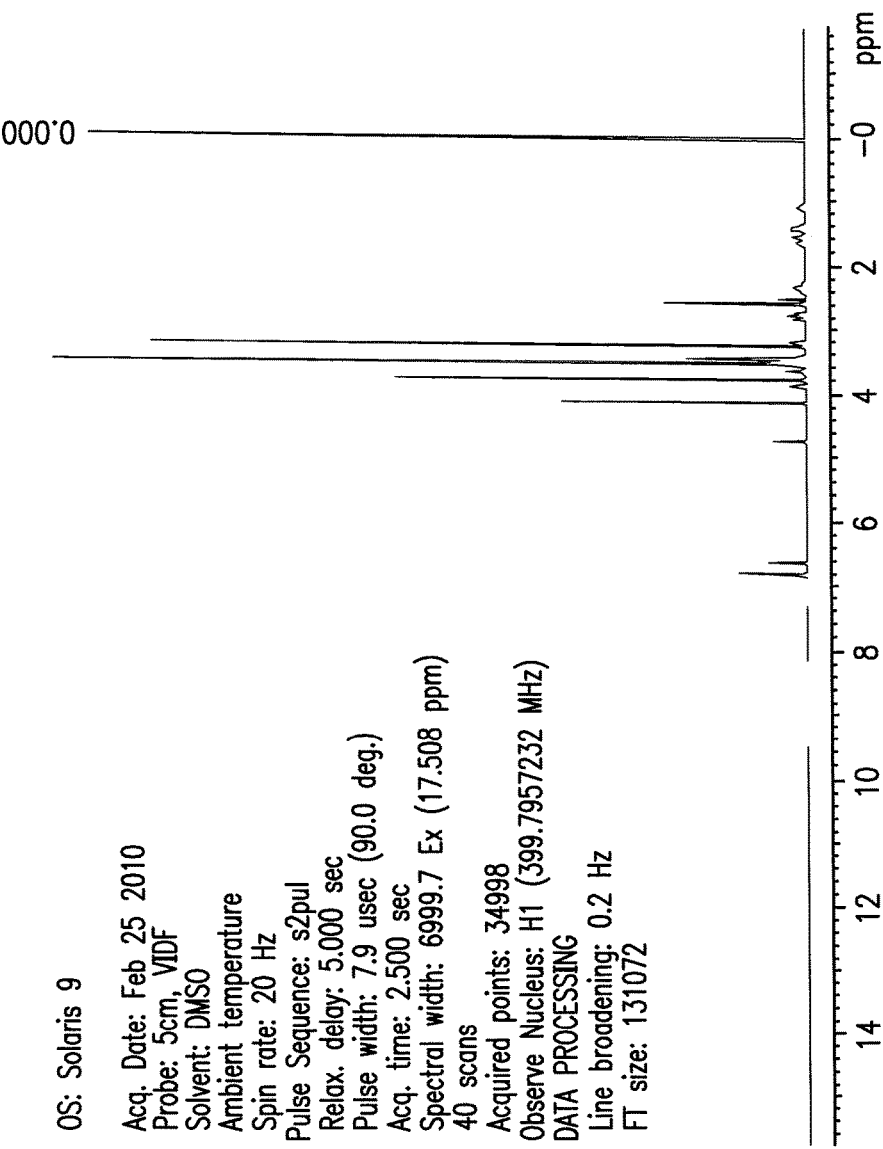
FIG. 8 is a 1H NMR of the solid α-6-mPEG$_6$-O-hydroxycodone D-tartaric acid salt prepared according to Example 1, taken in DMSO.
Figure 9:
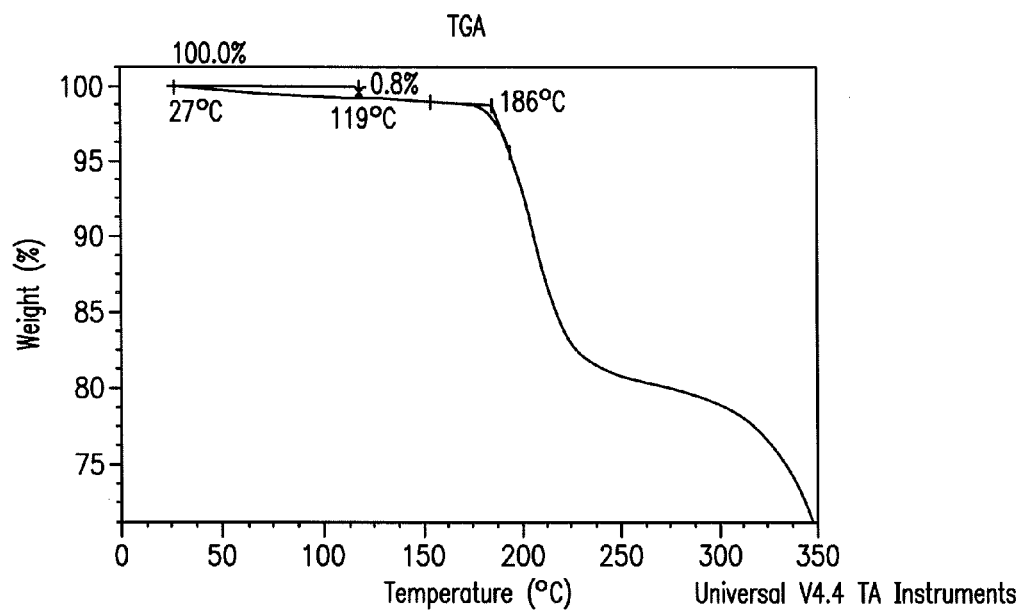
FIG. 9 is a thermogravimetirical analysis (TGA) of the solid α-6-mPEG$_6$-O-hydroxycodone D-tartaric acid salt prepared according to Example 1.
Figure 10:
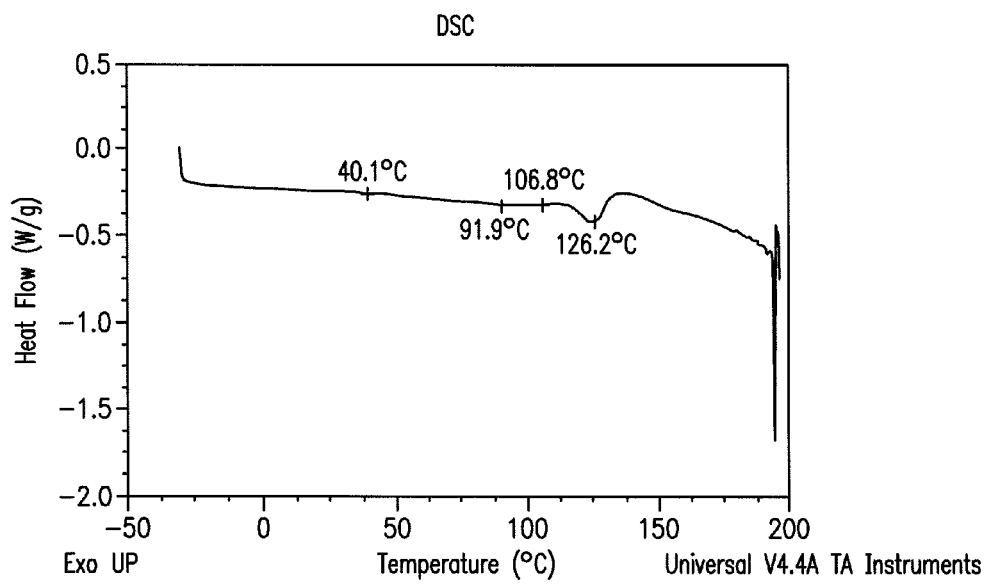
FIG. 10 is a differential scanning calorimetry (DSC) analysis of the solid α-6-mPEG$_6$-O-hydroxycodone D-tartaric acid salt prepared according to Example 1.

D-Tartaric Acid Salt:

To 200 mg of α-6-mPEG$_6$-O-hydroxycodone dissolved in THF (~200 mg/mL) was added D-tartaric acid solution (~50.5 mg in 200 μL MeOH, ~1.7M) dissolved in MeOH (clear solution), 1 mL EtOAc was added (clear solution), rotary evaporation yielded solids, 1 mL MTBE was added to the solids and stirred at room temperature for about 1 day. Solid α-6-mPEG$_6$-O-hydroxycodone D-tartaric acid salt was recovered by vacuum filtration (yield=~71%). FIG. 7 is an XRPD pattern of the D-tartaric acid salt. FIG. 8 is a $^1$H NMR of the D-tartaric acid salt taken in DMSO. FIG. 9 is a thermogravimetirical analysis (TGA) of the D-tartaric acid salt. FIG. 10 is a differential scanning calorimetry (DSC) analysis of the D-tartaric acid salt.

A focused crystallization screen was performed in an attempt to further crystallize those materials.

Example 2

Focused Crystallization Screen

Phosphate Salt:

Twenty experiments were performed in order to search for conditions that would provide a further crystalline material of the α-6-mPEG$_6$-O-hydroxycodone phosphoric acid salt. Experimental conditions are summarized in Table 2.

TABLE 2

| Solvent System | Conditions | Result |
|---|---|---|
| Ethyl Acetate (EtOAc) | Slurry at ~40° C. for ~5 days, vacuum filtration, blew N$_2$, | Tacky solids, XRPD same as FIG. 1 |
| Ethanol | Slurry and RT (room temperature), added EtOAc (ethyl acetate), stirred ~1 day, cloudy solution | — |
| Toluene | Attempted slow cooling at ~80° C., slurry at ~60° C. for ~5 days, stirred at ~95° C. for ~1 day (viscous material, cloudy), kept at RT for ~1 day (viscous, fine solids), vacuum filtered and washed with MTBE, vacuum filtration and vacuum oven for ~2 days | XRPD same as FIG. 1 |
| Acetone/Heptane (1:1) | Slurry at RT for ~4 hr (no visual solids, hazy solution) added heptane (white ppt), slurry at RT for ~5 days | Aggregates, XRPD same as FIG. 1 |
| Acetonitrile/ MeOH (9:1) | Slow cooling attempt in acetonitrile (ACN) at ~60° C. (cloudy solution), added minimal MeOH (clear solution), slow cooling to RT (slightly hazy) kept in refrigerator for ~5 days, kept in freezer for ~5 days (slightly hazy solution), no solid, fast evaporation yielded sticky solids, vacuum oven for ~2 days | Aggregates, XRPD same as FIG. 1 |
| Chloroform/ Ethyl Acetate | Vapor diffusion (solids), vacuum filtration, insufficient solids | — |
| Chloroform/ Isopropyl ether | Vapor diffusion, few solids collected | XRPD same as FIG. 1 |
| Chloroform/ heptane (9:1) | Vapor diffusion, solids formed, vacuum oven for ~1 day | XRPD same as FIG. 1 |
| Chloroform/ toluene (9:1) | Vapor diffusion, solids formed, vacuum oven for ~1 day | — |
| EtOH/Heptane (1:29) | Slurry at ~60° C. for ~5 days | XRPD same as FIG. 1 |
| EtOH/Hexanes | Vapor diffusion (solids), refrigerate for ~7 days (fine solids), vacuum filtration | — |
| Isopropyl alcohol/ water (19:1) | Stirred, few solids, fast evaporation, vacuum oven | — |
| Methanol/1,2 Dichloroethane (9:1) | Slow evaporation (tacky solids) vacuum oven ~1 day | XRPD same as FIG. 1 with additional peak |
| Methanol/tert-butyl methyl ether (MTBE) | Vapor diffusion, vacuum filtration | XRPD same as FIG. 1 |
| Methanol/ EtOAc (9:1) | Slow evaporation, vacuum oven for ~1 day | — |

TABLE 2-continued

| Solvent System | Conditions | Result |
| --- | --- | --- |
| Methanol/ EtOAc (9:1) | Slow evaporation, vacuum oven for ~1 day | XRPD same as FIG. 1 with additional peak |
| THF/water (19:1) | Slow cooling attempt from ~56 to RT (viscous mass), added MTBE, stirred for ~4 days (solvent evaporated, tacky solids), added MTBE, stirred for ~1 day, vacuum filtration (slow filtration) | XRPD same as FIG. 1 with additional peak |

Crystallization techniques included slurrying at ambient and elevated temperature, slow cooling, vapor diffusion, slow evaporation, and heat stress experiments. Experiments were designed to be performed over several days in order to have the highest chance of crystallization. The majority of experiments resulted in materials exhibiting the same XRPD pattern as that of FIG. 1. Three experiments (slow evaporation of methanol:1,2-dichloroethane (9:1) and methanol:ethyl acetate (9:1), and cooling from tetrahydrofuran:water (19:1) followed by a slurry in tert-butyl methyl ether) resulted in material exhibiting the same XRPD pattern, with greater resolution observed for peaks at ~15.0 and ~17.0 °2θ, such that a new broad peak is observed at ~16 °2θ. (FIG. 5). This material is likely the same phosphate salt, but with only slightly more order. No crystallization experiments resulted materials that appear to be significantly more crystalline than the starting material.

D-Tartrate Salt (Material B):

Thirteen experiments were performed for the crystallization of α-6-mPEG$_6$-O-hydroxycodone D-tartrate salt. Crystallization techniques included slurrying at subambient and elevated temperature, slow cooling, vapor diffusion, slow evaporation, and heat stress experiments. Experimental conditions are summarized in Table 3. All attempts to further crystallize the D-tartrate salt resulted in material similar to that observed in Example 1.

TABLE 3

| Solvent System | Conditions | Result |
| --- | --- | --- |
| Acetone | Slurry, cold room (very fine solids), added MTBE (white ppt) stirred in cold room for ~3 days (slightly viscous), vacuum filtration (deliquesced) | No Solid |
| Cumene | Slurry at ~80° C. for ~4 h (solids on wall), moved to −60° C. oil bath, stirred for 4 days, stirred at ~95° C. for ~1 day (viscous clump), stirred at ~110° C. for ~2 h (viscous mass), FC at RT (viscous mass) | No Solid |
| MeOH/1,2 dichloroethane (9:1) | Slow evaporation (sticky solids), vacuum oven at RT morphology for ~1 days | XRPD same as FIG. 7 |
| Nitromethane | Slow cooling ~80° C. to RT (clear solution), kept in refrigerator for ~1 day (clear solution), partial fast evaporation (slightly hazy solution), kept in refrigerator for ~4 days (slightly hazy solution); fast evaporation (tacky solids), vacuum oven at RT for ~1 day | XRPD same as FIG. 7 |
| THF | Slurry, cold room (viscous material), added heptane (white ppt) stirred in cold room for ~3 days (cloudy solution), vacuum filtration, blew N$_2$ (deliquescing, very few tacky solids), vacuum oven at RT for ~3 days | XRPD same as FIG. 7 |
| Chloroform/ Isopropyl ether | Vapor diffusion, vacuum filtration, blew N$_2$ | XRPD same as FIG. 7 |
| Chloroform/ EtOAc | Vapor diffusion, vacuum filtration, blew N$_2$ | XRPD same as FIG. 7 |
| EtOAc/EtOH (9:1) | Slurry ~50° C. for ~6 days (viscous material), kept at RT for ~2 days (viscous material), added heptane (viscous material), stirred at RT for ~2 days (solids), vacuum filtration, blew N$_2$ (slightly tacky solids), vacuum oven at RT for ~3 days | XRPD same as FIG. 7 |
| MeOH/MTBE | Vapor diffusion (solids), vacuum filtration (tacky solids), vacuum oven at RT for ~1 day | XRPD same as FIG. 7 |
| THF/Heptane (1:9) | Slurry ~50° C. for −6 days (solvent evaporated), added more solvent, stirred at ~50° C. for ~1 day, vacuum filtration (slightly tacky solids), blew N$_2$ | XRPD same as FIG. 7 |
| "" | Heat stress ~60° C. for ~6 days | |
| "" | vacuum oven ~45° C. for ~3 days | |

Example 3

Figure 11:
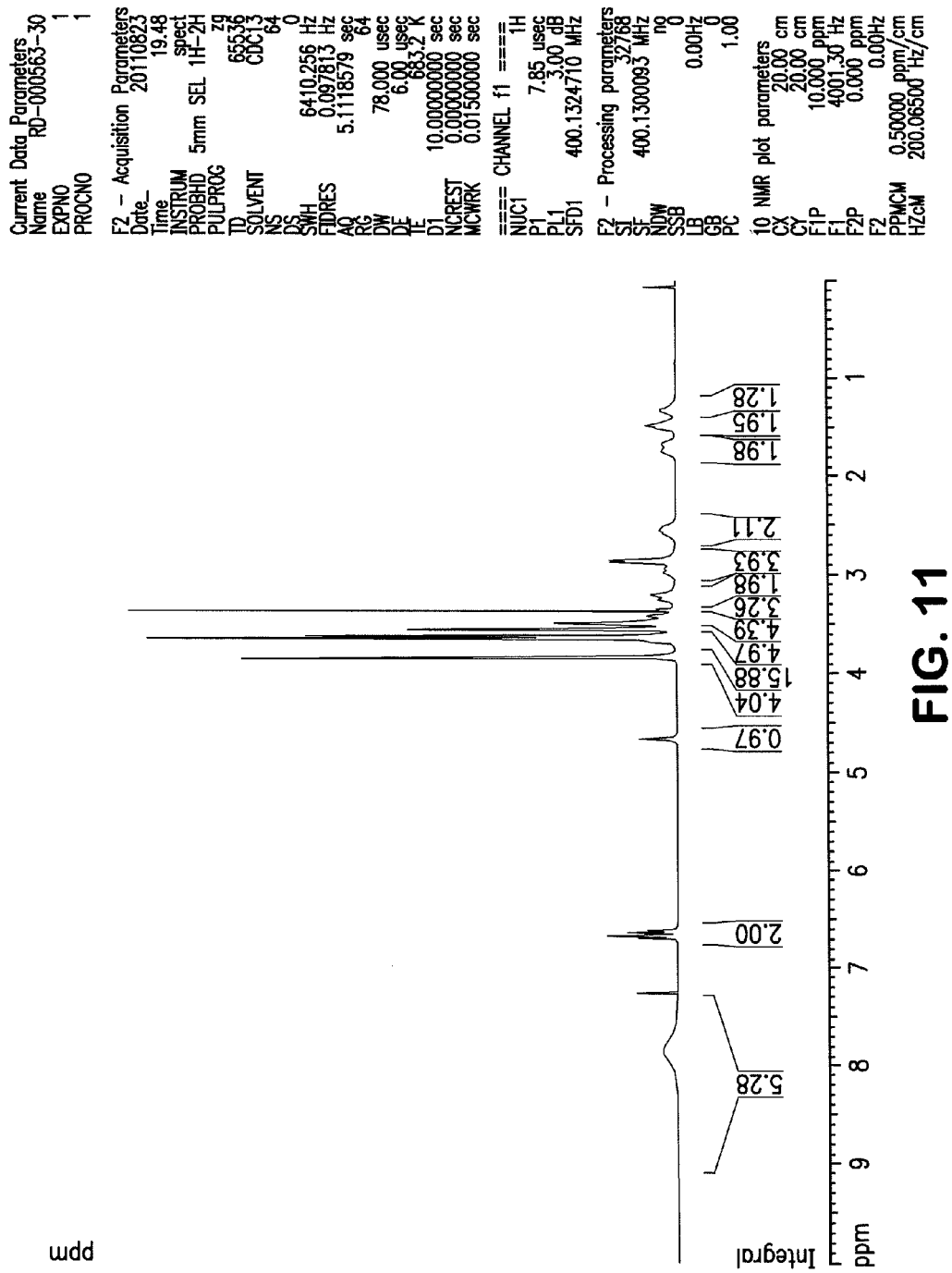
FIG. 11 is a 1H NMR of the solid α-6-mPEG$_6$-O-hydroxycodone phosphate salt prepared according to Example 3, taken in CDCl$_3$.

Large Scale (Kilogram Scale) Preparation of Alpha 6-mPEG$_6$-O-Hydroxycodone Phosphate Salt A solution of α-6-mPEG$_6$-O-hydroxycodone was prepared in a mixture of methanol and tert-butyl methyl ether (2:1, 2 volumes) at 30° C. A solution of phosphoric acid (85% aqueous, 1.05 eq) was prepared in a mixture of methanol and tert-butyl methyl ether (2:1, 1.2 volumes) at 20° C. The solutions were combined, maintaining a temperature of 30-50° C., resulting in the formation of dissolved α-6-mPEG$_6$-O-hydroxycodone phosphate. This salt solution was adjusted to 40° C., and gradually transferred over the course of 1-3 hours into a solution of heptanes and tert-butyl methyl ether (4:1, 14 volumes) maintained at 45° C. During the transfer, α-6-mPEG$_6$-O-hydroxycodone phosphate precipitated from the combined streams. The resulting slurry was cooled to 20° C. and agitation was ceased, permitting the solids to settle. The supernate was decanted, and heptanes (6 volumes) were added to the solids. The solids were slurried for at least one hour at 30° C., after which the slurry was cooled to 20° C. Again agitation was ceased, the solids were allowed to settle, and the supernate was decanted. Fresh heptanes were added to the solids, which were again slurried for at least one hour at 30° C. The slurry was cooled to 20° C., filtered, and washed with fresh heptanes (2 volumes). The wet cake was transferred to a vacuum chamber and dried at ambient temperature for at least 48 hours, to afford α-6-mPEG$_6$-O-hydroxycodone phosphate, as a slightly waxy, hygroscopic powder, in 90+% yield. A $^1$H NMR of the product is listed in FIG. 11. An XRPD plot of a solid made according to this Example on a 100 g scale is shown in FIG. 16. The solid form prepared according to this Example has a melting point in the range of about 175-177° C.

Example 4

Large Scale (Gram Scale) Preparation of Alpha 6-mPEG$_6$-O-Hydroxycodone D-Tartrate Salt A solution of α-6-mPEG$_6$-O-hydroxycodone was prepared in tetrahydrofuran (2 volumes) at 20° C. A solution of D-tartaric acid was likewise prepared in tetrahydrofuran (2 volumes) at 50° C. The solution of α-6-mPEG$_6$-O-hydroxycodone was gradually introduced into the solution of D-tartaric acid, over the course of 30 minutes. The resulting solution was stirred for 2 hours, maintaining a temperature at 50° C. Heptanes (6 volumes) were introduced over the course of 30 minutes, while continuing to maintain temperature. The product (α-6-mPEG$_6$-O-hydroxycodone D-tartrate) precipitates during the heptanes addition. The resulting slurry was stirred for 2 hours at 50° C., and then allowed to cool gradually to 20° C. The slurry was filtered, washed with heptanes (2 volumes), and transferred to a desiccating vacuum chamber (containing P$_2$O$_5$) to dry at ambient temperature for at least 12 hours. The product was recovered as a deliquescent white powder in 90+% yield. FIG. 12 is a XRPD pattern of the α-6-mPEG$_6$-O-hydroxycodone D-tartrate salt prepared according to this method.

Example 5

Preparation of Alpha-6-mPEG$_6$-O-Hydroxycodone Free Base Tablets

Film coated tables comprising α-6-mPEG$_6$-O-hydroxycodone free base were prepared as follows. Table 4 below reports the components in each tablet prepared*. The "amount" refers to the amount of a particular component as listed in Table 4 for the particular trial being described.

Preparation of Tablet 2 (Trial 2, 50 mg α-6-mPEG$_6$-O-Hydroxycodone Free Base):

The amount (i.e. the amount listed in Trial 2 of Table 4) of citric acid was dissolved in water to form citric acid solution. The amount α-6-mPEG$_6$-O-hydroxycodone free base was dissolved in citric acid solution to form an α-6-mPEG$_6$-O-hydroxycodone free base/citric acid solution. The amount of polyvinyl pyrolidone (PVP), USP was dissolved in water to form PVP solution.

The amounts of lactose monohydrate, microcrystalline cellulose, and croscarmellose sodium, were screened through #20 mesh, transferred to the bowl of a high shear granulator, and mixed for about five minutes with impeller on at 250 RPM. While the powders were mixing, the mixture was granulated with the previously prepared α-6-mPEG$_6$-O-hydroxycodone free base/citric acid solution followed by the PVP solution with impeller at 500 RPM and chopper at 1200 RPM. Additional water was added, with continued kneading, to produce a wet mass of suitable consistency.

The wet granules were then dried in a fluid bed dryer with an inlet setting of 50° C. until loss of drying (LOD) less than 3% is obtained. The dried granules were passed through a #16 mesh screen. The dried and screened granules were mixed with the quantities of extra granular excipients (cross carmellose sodium and colloidal silicon dioxide) that were pre-screened through #20 mesh for twelve minutes in a V blender. The quantity of magnesium stearate was screened through #40 mesh and added to contents in V blender and mixed for three minutes to form final blend for tablet compression.

The final blend is compressed on a rotary tablet press at a target weight of 350 mg to result into core tablets having hardness of ~12 Kp, friability of 0.113%, and disintegrating of ~14 minutes.

A 20% w/w film coating dispersion solution was prepared and sprayed onto core tablets in a perforated film coating pan to a theoretical weight gain of ~5%. The tablets were cooled

TABLE 4

| Ingredient | 50 mg Tablet (mg/tablet) | 50 mg Tablet (mg/tablet) | 50 mg Tablet (mg/tablet) | 50 mg Tablet (mg/tablet) |
|---|---|---|---|---|
| Trial # | 1 | 2 | 3 | 4 |
| Intra Granular | | | | |
| α-6-mPEG$_6$-O-hydroxycodone free base | 50.0 | 50.0 | 50.0 | 50.0 |
| Lactose Monohydrate, NF (Pharmtose ® 450M) | 125.0 | 87.5 | 87.5 | — |
| Microcrystalline Cellulose (Avicel ® PH101) | 57.50 | 154.0 | 174.0 | 154.0 |
| Croscarmellose sodium, USP/NF (Ac-Di-Sol ®) | 6.25 | 8.75 | 8.75 | 8.75 |
| Dibasic Calcium phosphate anhydrous, NF(Fujicalin ®) | — | — | — | 87.5 |
| Citric acid anhydrous | — | 20.0 | — | 20.0 |
| Polyvinyl pyrolidone, USP (Povidone) | — | 14.0 | 14.0 | 14.0 |
| Extra Granular | | | | |
| Microcrystalline Cellulose (Avicel ® PH102) | 50.0 | — | — | — |
| Lactose Monohydrate, NF (Super Tab ®) | 50.0 | — | — | — |
| Croscarmellose sodium, USP/NF (Ac-Di-Sol ®) | 6.25 | 8.75 | 8.75 | 8.75 |
| Colloidal Silicon Dioxide, USP/NF (Cabosil ® M5) | 2.50 | 3.50 | 3.50 | 3.50 |
| Stearic Acid, NF | 1.25 | — | — | — |
| Magnesium stearate (veg. grade) | 1.25 | 3.50 | 3.50 | 3.50 |
| Core tablet weight (mg) | 350.0 | 350.0 | 350.0 | 350.0 |
| Film coating | | | | |
| Opadry ® II 85F18422 White | 12.5 | 17..5 | 17.5 | 17.5 |
| Film coated tablet weight (mg) | 362.5 | 367.5 | 367.5 | 367.5 |
| Drug loading | 13.8 | 13.6 | 13.6 | 13.6 |

* Tablets of trials 1 and 3 were not prepared due to poor flow properties of the composition to room temperature and discharged from coating pan into bulk containers. The film coated tablets were tested for assay, drug dissolution, and content uniformity. Results of coated tablet testing are summarized below in Table 5.

TABLE 5

TESTING OF 50 MG ALPHA-6-MPEG$_6$-O-HYDROXYCODONE FREE BASE FILM COATED TABLET 2

| Attribute | Tablet 2 |
|---|---|
| Assay | 102.8 |
| Content Uniformity (n = 10) | Mean: 99.2%; % RSD: 1.6 |
| | Range: 96.2-101.7 |
| Dissolution[1] (n = 6) | |
| % mean dissolved at 5 minutes | 12.1 |
| % mean dissolved at 10 minutes | 32.6 |
| % mean dissolved at 15 minutes | 53.4 |
| % mean dissolved at 30 minutes | 95.3 |

[1]Dissolution Conditions: 0.1N HCl, 900 ml, Type II (paddle) apparatus, 50 RPM

Preparation of Tablet 4 (50 mg α-6-mPEG$_6$-O-Hydroxycodone Free Base):

The amount (i.e. the amount listed in Trial 4 of Table 4) of polyvinyl pyrolidone (PVP) was dissolved in water to form PVP solution. The amount of citric acid was dissolved in water to form citric acid solution. The amount of α-6-mPEG$_6$-O-hydroxycodone free base was dissolved in citric acid solution to form an α-6-mPEG$_6$-O-hydroxycodone free base/citric acid solution.

The amounts of dibasic calcium phosphate anhydrous, microcrystalline cellulose, and croscarmellose sodium, were screened through #20 mesh, transferred to the bowl of a high shear granulator, and mixed for five minutes with impeller on at 250 RPM. While the powders were mixing, the mixture was granulated with previously prepared α-6-mPEG$_6$-O-hydroxycodone free base-citric acid solution followed by the PVP solution with impeller at 500 RPM and chopper at 1200 RPM. Additional water was added, with continued kneading, to produce a wet mass of suitable consistency.

The wet granules were then dried in a fluid bed dryer with an inlet setting of 50° C. until loss of drying (LOD) less than 3% was obtained. The dried granules were passed through a #16 mesh screen. The dried and screened granules were mixed with the quantities of extra granular excipients (cross carmellose sodium and colloidal silicon dioxide) that were pre-screened through #20 mesh for twelve minutes in a V blender. The quantity of magnesium stearate was screened through #40 mesh and added to contents in V blender and mixed for three minutes to form final blend for tablet compression.

The final blend was compressed on a rotary tablet press at a target weight of 350.0 mg to result in core tablets having hardness of ~6 Kp, friability of 0%, and disintegration time of ~8 minutes.

A 20% w/w film coating dispersion solution was prepared and sprayed onto core tablets in a perforated film coating pan to a theoretical weight gain of ~5%. The tablets were cooled to room temperature and discharged from coating pan into bulk containers. The film coated tablets were tested for assay, drug dissolution, and content uniformity. Results of coated tablets testing are summarized below in Table 6.

TABLE 6

TESTING OF 50 MG ALPHA-6-MPEG$_6$-O-HYDROXYCODONE FREE BASE FILM COATED TABLET 2

| Attribute | Tablet 4 |
|---|---|
| Assay | 102.1 |
| Content Uniformity (n = 10) | Mean: 100.6%; % RSD: 1.2 |
| | Range: 98.8-102.7 |
| Dissolution[1] (n = 6) | |
| % mean dissolved at 5 minutes | 25.9 |
| % mean dissolved at 10 minutes | 66.3 |
| % mean dissolved at 15 minutes | 91.1 |
| % mean dissolved at 30 minutes | 99.0 |

[1]Dissolution Conditions: 0.1N HCl, 900 ml, Type II (paddle) apparatus, 50 RPM

Example 6

Preparation of Solid Alpha-6-mPEG$_6$-O-Hydroxycodone Phosphate Salt Tablets

Film coated tablets comprising solid α-6-mPEG$_6$-O-hydroxycodone phosphate were prepared as follows. The solid α-6-mPEG$_6$-O-hydroxycodone phosphate includes the solid α-6-mPEG$_6$-O-hydroxycodone phosphate salt forms described herein. Table 7 below reports the components in each tablet prepared. The "amount" refers to the amount of each component listed in Table 7 for each referenced tablet.

TABLE 7

| Ingredient | 100 mg Tablet (mg/tablet) | 200 mg Tablet (mg/tablet) | 400 mg Tablet (mg/tablet) |
|---|---|---|---|
| Trial # | 1 | 2 | 3 |
| Intra Granular | | | |
| solid α-6-mPEG$_6$-O-hydroxycodone phosphate (free base) | 116.25 (100.00) | 232.50 (200.00) | 465.00 (400.00) |
| Dibasic Calcium phosphate anhydrous, NF(Fujicalin ®) | 223.54 | 223.54 | 223.54 |
| Microcrystalline Cellulose (Avicel ® PH101) | 418.91 | 302.66 | 0.00 |
| Croscarmellose sodium, USP/NF (Ac-Di-Sol ®) | 33.04 | 33.04 | 32.40 |
| Colloidal Silicon Dioxide, USP/NF (Cabosil ® M5) | 27.13 | 54.25 | 108.50 |
| Polyvinyl pyrolidone, USP (Povidone) | 40.00 | 19.72 | 19.36 |
| Extra Granular | | | |
| Microcrystalline Cellulose (Avicel ® PH102) | 208.61 | 211.77 | 0.00 |
| Dibasic Calcium phosphate anhydrous, NF(Fujicalin ®) | 0.00 | 0.00 | 223.54 |
| Citric acid monohydrate, NF | 40.00 | 80.00 | 160.00 |
| Croscarmellose sodium, USP/NF (Ac-Di-Sol ®) | 16.20 | 16.20 | 32.40 |
| Colloidal silicon dioxide, USP/NF (Cabosil ® M5) | 13.16 | 13.16 | 15.50 |
| Magnesium stearate (veg. grade) | 13.16 | 13.16 | 15.50 |
| Core tablet weight (mg) | 1150.00 | 1200.00 | 1295.74 |

TABLE 7-continued

| Ingredient | 100 mg Tablet (mg/tablet) | 200 mg Tablet (mg/tablet) | 400 mg Tablet (mg/tablet |
|---|---|---|---|
| Film coating | | | |
| Opadry ® II 85F105039 Blue | 46.00 | 48.00 | 51.83 |
| Film coated tablet weight (mg) | 1196.00 | 1248.00 | 1347.57 |
| Drug loading (as salt) | 9.7% | 18.6% | 34.5% |
| Drug loading (as free base) | 8.4% | 16.0% | 29.7% |

100 mg α-6-mPEG$_6$-O-Hydroxycodone Phosphate Tablets (Trial 1):

The amount of polyvinyl pyrolidone (PVP) was dissolved in water to form a PVP solution. The amounts of solid α-6-mPEG$_6$-O-hydroxycodone phosphate salt were screened through #14 mesh screen and transferred to the bowl of a high shear granulator. Dibasic calcium phosphate anhydrous, microcrystalline cellulose, croscarmellose sodium, and colloidal silicon dioxide were screened through #20 mesh and transferred to the bowl of a high shear granulator. The contents in the bowl of the high shear granulator were mixed for five minutes with impeller on at 250 RPM. While the powders were mixing, the mixture was granulated with the previously prepared PVP solution with an impeller at 500 RPM and chopper at 1200 RPM. Additional water was added, with continued kneading, to produce a wet mass of suitable consistency.

The wet granules were then dried in a fluid bed dryer with an inlet setting of ~50° C. until loss of drying (LOD) less than 3% is obtained. The dried granules were passed through a #16 mesh screen. The dried and screened granules were mixed with the quantities of extra granular excipients (microcrystalline cellulose, citric acid monohydrate, cross carmellose sodium, and colloidal silicon dioxide) that were pre-screened through #20 mesh for twelve (12) minutes in a V blender. The quantity of magnesium stearate was screened through #40 mesh and added the contents in V blender and mixed for three minutes to form the final blend for tablet compression.

The final blend was compressed on a rotary tablet press at a target weight of 1150.0 mg to result into core tablets having hardness of ~19 Kp, friability of 0.07%, and disintegration time of ~9 min.

A 20% w/w film coating dispersion was prepared and sprayed onto the core tablets in a perforated film coating pan to a theoretical weight gain of ~4%. The tablets were cooled to room temperature and discharged from coating pan into bulk containers. The film coated tablets were tested for assay, drug dissolution, and content uniformity. Results of coated tablet testing are summarized below in Table 8.

TABLE 8

TESTING OF FILM COATED 100 MG ALPHA-6-MPEG$_6$-O-HYDROXYCODONE PHOSPHATE TABLETS

| Attribute | 100 mg Tablets |
|---|---|
| Assay | 99.4% |
| Content Uniformity (n = 10) | |
| Mean; % RSD | 99.7%; 1.3% |
| Range | 98.1-101.9% |

TABLE 8-continued

TESTING OF FILM COATED 100 MG ALPHA-6-MPEG$_6$-O-HYDROXYCODONE PHOSPHATE TABLETS

| | 100 mg Tablets |
|---|---|
| Dissolution[1] (n = 6) | |
| mean dissolved at 5 minutes | 23.8% |
| mean dissolved at 10 minutes | 60.2% |
| mean dissolved at 15 minutes | 80.5% |
| mean dissolved at 30 minutes | 85.6% |
| mean dissolved at 45 minutes | 86.9% |
| mean dissolved at 60 minutes | 88.3% |

[1]Dissolution Conditions: 0.1N HCl, 900 ml, Type II (paddle) apparatus, 50 RPM 200 mg α-6-mPEG$_6$-O-Hydroxycodone Phosphate Tablets (Trial 2):

The amount of polyvinyl pyrolidone (PVP) was dissolved in water to form a PVP solution. The amount of solid α-6-mPEG$_6$-O-hydroxycodone phosphate salt was screened through #14 mesh screen and transferred to the bowl of high shear granulator. Dibasic calcium phosphate anhydrous, microcrystalline cellulose, croscarmellose sodium, and colloidal silicon sioxide were screened through #20 mesh and transferred to the bowl of as high shear granulator. The contents in the bowl of the high shear granulator were mixed for five minutes with an impeller on at 250 RPM. While the powders were mixing, the mixture was granulated with the previously prepared PVP solution with the impeller at 500 RPM and chopper at 1200 RPM. Additional water was added, with continued kneading, to produce a wet mass of suitable consistency.

The wet granules were then dried in a fluid bed dryer with an inlet setting of ~50° C. until loss of drying (LOD) less than 3% was obtained. The dried granules were passed through a #16 mesh screen. The dried and screened granules were mixed with quantities of extra granular excipients (microcrystalline cellulose, citric acid monohydrate, cross carmellose sodium, and colloidal silicon dioxide) that were pre-screened through #20 mesh for twelve minutes in a V blender. The quantity of magnesium stearate was screened through #40 mesh and the contents were added in V blender and mixed for three minutes to form final blend for tablet compression.

The final blend was compressed on a rotary tablet press at a target weight of 1200.0 mg to result into core tablets having hardness of ~19 Kp, friability of 0.06%, and disintegration time of ~8 min.

A 20% w/w film coating dispersion was prepared and sprayed onto the core tablets in a perforated film coating pan to a theoretical weight gain of ~4%. The tablets were cooled to room temperature and discharged from coating pan into bulk containers. The film coated tablets were tested for assay, drug dissolution, and content uniformity. Results of coated tablet testing are summarized below in Table 9.

TABLE 9

TESTING OF FILM COATED 200 MG ALPHA-6-MPEG$_6$-O-HYDROXYCODONE PHOSPHATE TABLETS

| Attribute | 200 mg Tablets |
|---|---|
| Assay | 99.3% |
| Content Uniformity (n = 10) | |
| Mean; % RSD | 97.8%; 1.2% |
| Range | 95.7-99.8% |

TABLE 9-continued

TESTING OF FILM COATED 200 MG ALPHA-6-
MPEG$_6$-O-HYDROXYCODONE PHOSPHATE TABLETS

| | 200 mg Tablets |
|---|---|
| Dissolution[1] (n = 6) | |
| mean dissolved at 5 minutes | 18.6% |
| mean dissolved at 10 minutes | 54.7% |
| mean dissolved at 15 minutes | 75.0% |
| mean dissolved at 30 minutes | 87.9% |
| mean dissolved at 45 minutes | 89.6% |
| mean dissolved at 60 minutes | 90.9% |

[1]Dissolution Conditions: 0.1N HCl, 900 ml, Type II (paddle) apparatus, 50 RPM 400 mg α-6-mPEG$_6$-O-Hydroxycodone Phosphate Tablets (Trial 3):

The amount of polyvinyl pyrolidone (PVP) was dissolved in water to form a PVP solution. The amount of solid α-6-mPEG$_6$-O-hydroxycodone phosphate salt were screened through #14 mesh screen and transferred to the bowl of a high shear granulator. Dibasic calcium phosphate anhydrous, croscarmellose sodium, and colloidal silicon dioxide were screened through #20 mesh and transferred to the bowl of a high shear granulator. The contents in the bowl of high shear granulator were mixed for five minutes with impeller on at 250 RPM. While the powders were mixing, the mixture was granulated with the previously prepared PVP solution with impeller at 500 RPM and chopper at 1200 RPM. Additional water was added, with continued kneading, to produce a wet mass of suitable consistency.

The wet granules were then dried in a fluid bed dryer with an inlet setting of ~50° C. until loss of drying (LOD) less than 3% is obtained. The dried granules were passed through a #16 mesh screen. The dried and screened granules were mixed with the quantities of extra granular excipients (dibasic calcium phosphate anhydrous, citric acid monohydrate, cross carmellose sodium, and colloidal silicon dioxide) that were pre-screened through #20 mesh for twelve minutes in a V blender. The quantity of magnesium stearate was screened through #40 mesh and added to contents in V blender and mixed for three minutes to form final blend for tablet compression.

The final blend was compressed on a rotary tablet press at a target weight of 1295.7 mg to result into core tablets having hardness of ~18 Kp, friability of 0.04%, and disintegration time of ~12 min.

A 20% w/w film coating dispersion was prepared and sprayed onto the core tablets in a perforated film coating pan to a theoretical weight gain of ~4%. The tablets were cooled to room temperature and discharged from coating pan into bulk containers. The film coated tablets were tested for assay, drug dissolution, and content uniformity. Results of coated tablet testing are summarized below in Table 10.

TABLE 10

TESTING OF FILM COATED 400 MG ALPHA-6-
MPEG$_6$-O-HYDROXYCODONE PHOSPHATE TABLETS

| Attribute | 400 mg Tablets, |
|---|---|
| Assay | 95.0% |
| Content Uniformity (n = 10) | |
| Mean; % RSD | 96.6%; 3.4% |
| Range | 91.5-102.8% |

TABLE 10-continued

TESTING OF FILM COATED 400 MG ALPHA-6-
MPEG$_6$-O-HYDROXYCODONE PHOSPHATE TABLETS

| | 400 mg Tablets, |
|---|---|
| Dissolution[1] (n = 6) | |
| mean dissolved at 5 minutes | 9.0% |
| mean dissolved at 10 minutes | 28.6% |
| mean dissolved at 15 minutes | 47.6% |
| mean dissolved at 30 minutes | 88.0% |
| mean dissolved at 45 minutes | 97.2% |
| mean dissolved at 60 minutes | 99.4% |

[1]Dissolution Conditions: 0.1N HCl, 900 ml, Type II (paddle) apparatus, 50 RPM

As reported in Table 7, tablets comprising solid α-6-mPEG$_6$-O-hydroxycodone phosphate have been prepared that have a drug loading of at least about 34.5 percent (Table 7, Trial 3). While tablets were prepared using the free base of α-6-mPEG$_6$-O-hydroxycodone, the maximum drug loading for those tablets was about 14 percent. Tablets of different weights with drug loadings similar to those of Table 7, Trial 3, may be prepared in a similar manner. As such, use of the solid α-6-mPEG$_6$-O-hydroxycodone phosphate salt in tablets results in an increased drug loading. Practical implications of an increased drug loading are understood to those of skill in the art and include, among other things, a reduced tablet size, reduced cost of goods, and increased throughput. Reduced tablet size may also help with patient compliance. Further, the reduction in size may allow for the addition of other beneficial excipients.

Example 7

Figure 13:
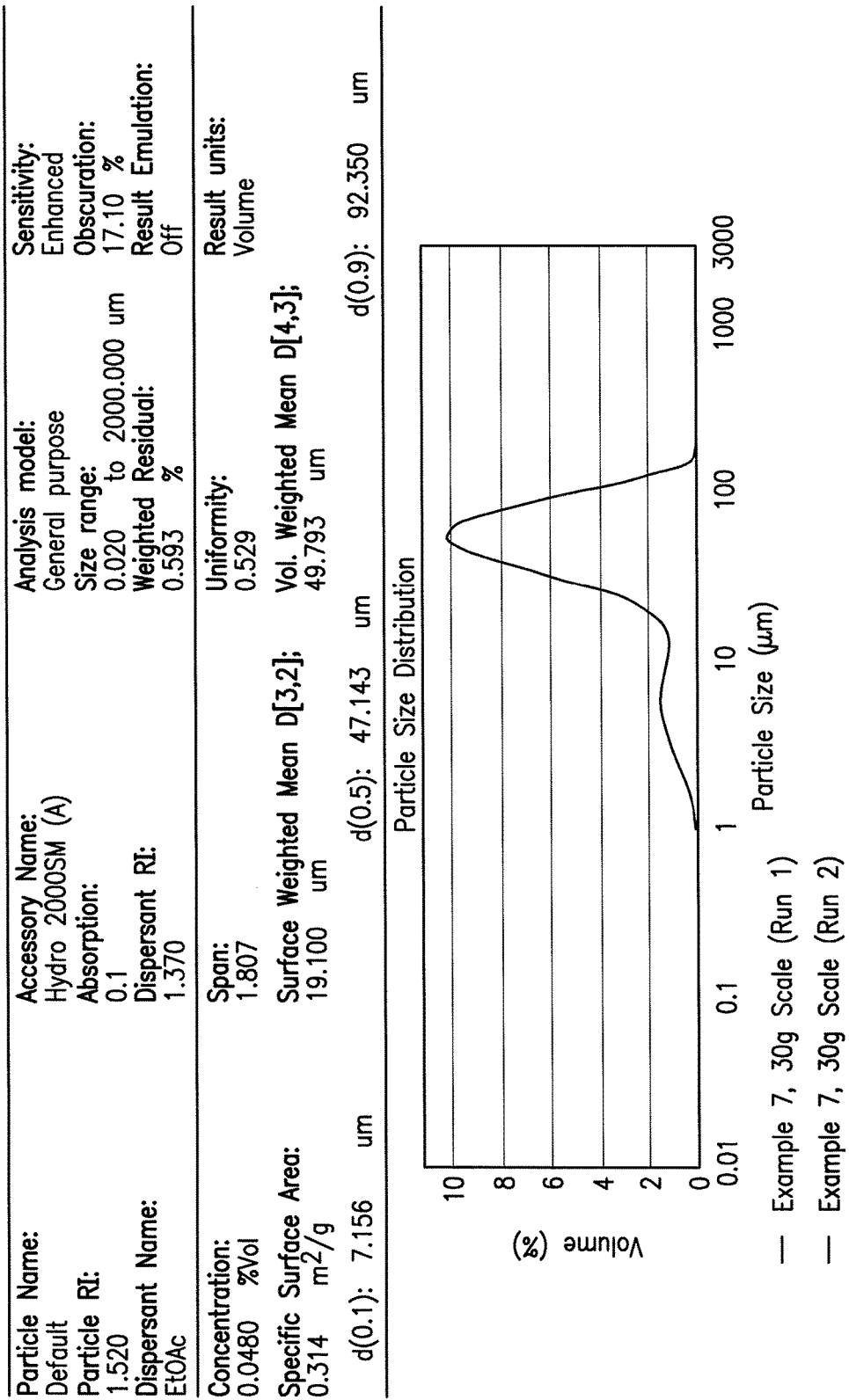
FIG. 13 is a plot of the particle size distribution for a 30 g lot of the α-6-mPEG$_6$-O-hydroxycodone phosphate salt prepared according to Example 7.
Figure 14:
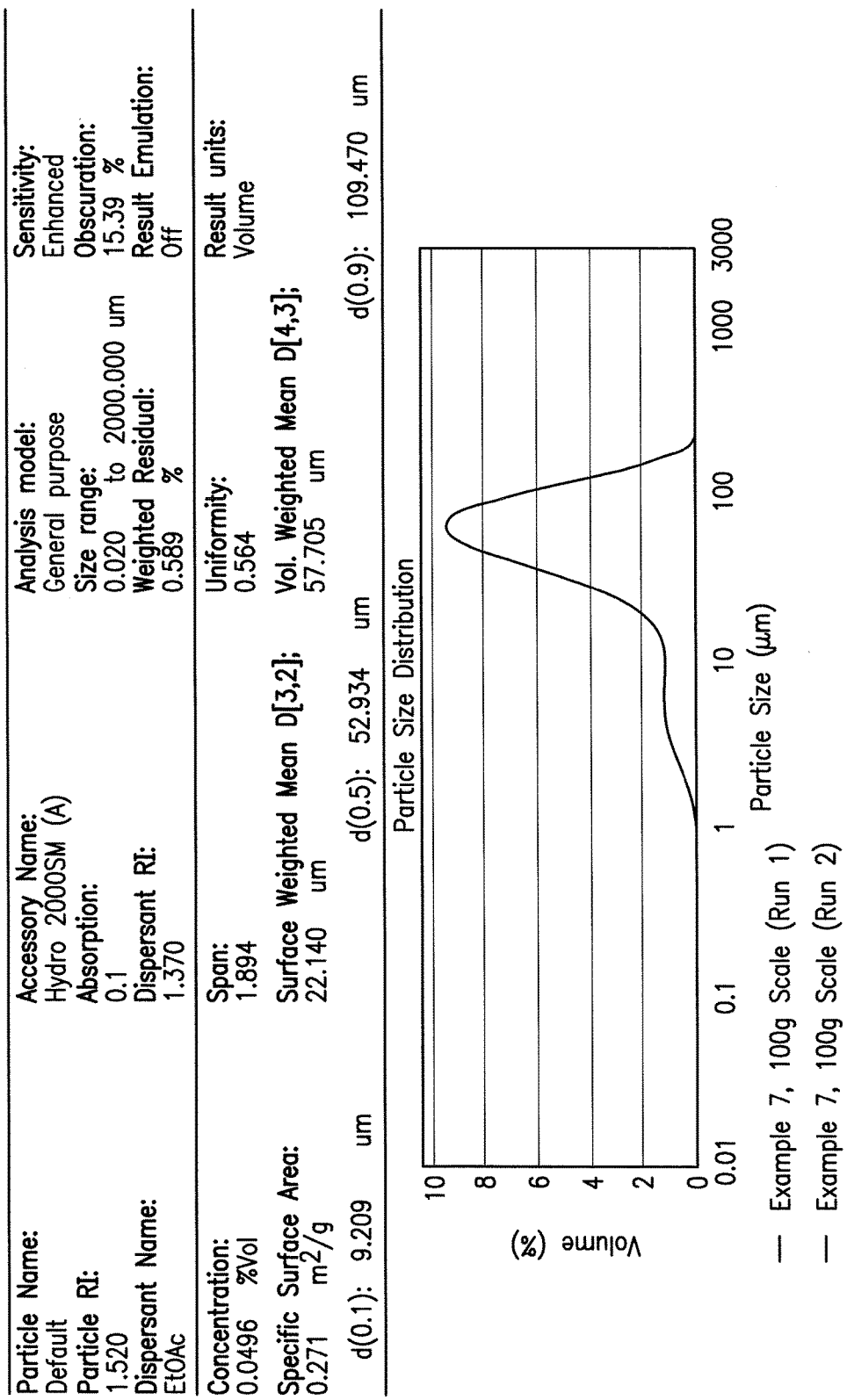
FIG. 14 is a plot of the particle size distribution for a 100 g lot of the α-6-mPEG$_6$-O-hydroxycodone phosphate salt prepared according to Example 7.
Figure 15:
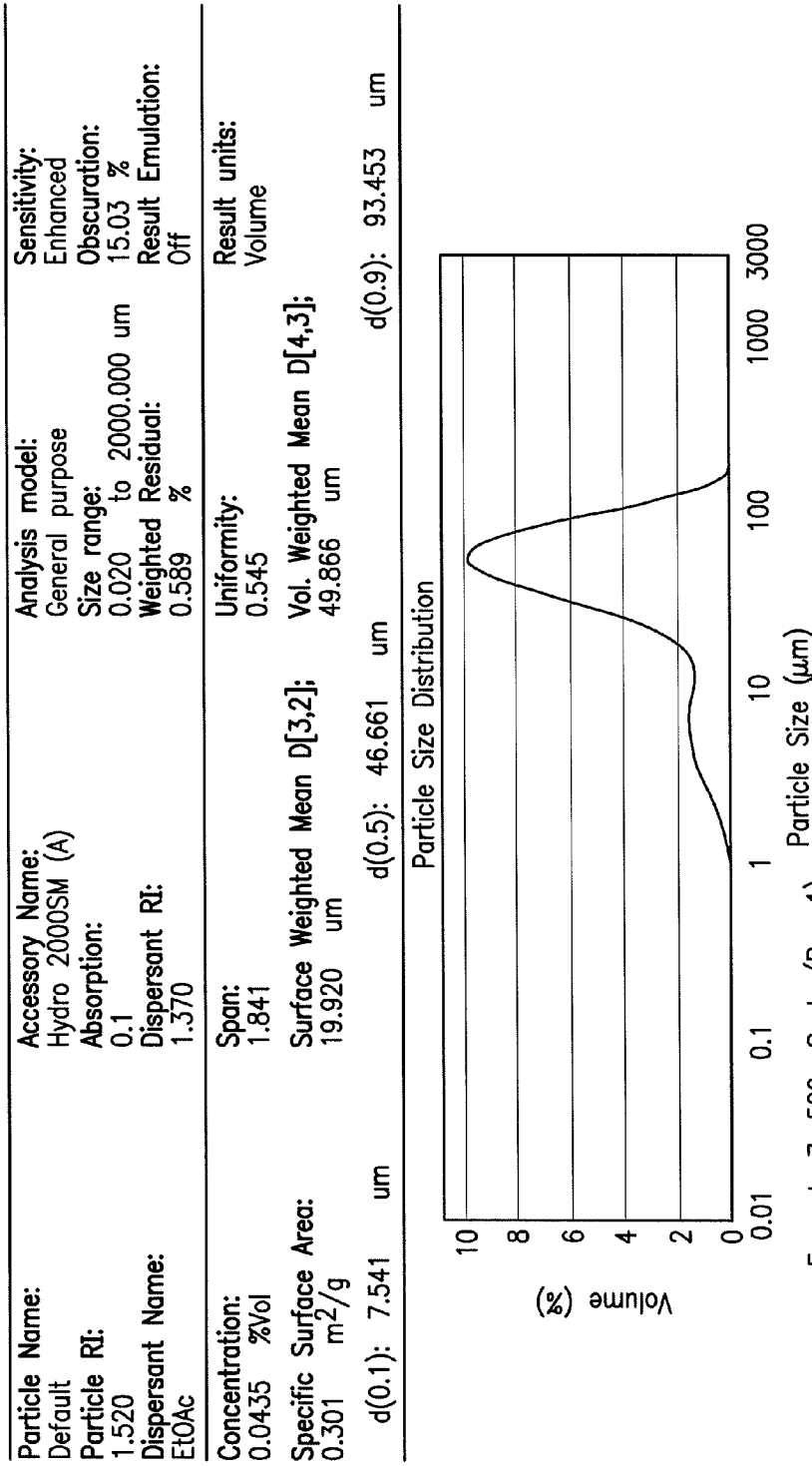
FIG. 15 is a plot of the particle size distribution for a 520 g lot of the α-6-mPEG$_6$-O-hydroxycodone phosphate salt prepared according to Example 7.

Alternative Preparation of Alpha 6-mPEG$_6$-O-Hydroxycodone Phosphate Salt 27.22 g of freebase alpha-6-mPEG$_6$-O-hydroxycodone was added to a 250 mL jacketed flask. The flask was equipped with a nitrogen inlet, mechanical stirrer and temperature probe connected to a digital read-out. 163 mL of tBME (methyl tert-butyl ether):heptane (5:1 vol:vol) was added to make a homogeneous solution at 15° C. Aqueous phosphoric acid (3103 μL of 85+%) was added over 1 hr at 10 minutes intervals. During the first addition, the initially formed solids were long strings and agitation helped to transform fine solid in matter of seconds. Exothermic temperature spikes occurred; the range of these increases was 8-10° C. observed during the initial 5 added portions. During the 6th and 7th added portion the temperature spike was reduced substantially to increments of a Celsius degree. After 2 hours the slurry was filtered. The filtration rate was instantaneous with no solvent retention. The wet cake was washed with 90 mL tBME (2×45 mL) and set to dry at ambient temperature overnight inside a vacuum oven. The isolated 30.57 g of white solid (96.5% isolated yield) was filtered. The solid after delumping with spatula was free flowing. The % LOD of the wet cake was at 43.2%. HPLC purity was at 98.6%. Bulk density was 0.3276 g/mL, tap density was 0.3931 g/mL, and the Hausner ratio was 1.20. XRPD conformed to the salt prepared according to Example 3. FIG. 16 depicts various XRPD scans for the salt prepared according to Example 7 on a 30 g, 100 g, and 520 g scale and a salt prepared according to Example 3 on a 100 g scale. XRPD patterns were obtained using a Bruker D8 Advance equipped with a Cu Kα radiation source (1.54 Å), a 9-position sample holder and a LYNXEYE Super Speed Detector. Typically, the duration of each scan was 180 seconds and the 2θ range was 4 to 40°. Samples were placed on zero-background, silicon plate holders. Additional characteristics of the salts prepared according to the present Example are listed in Table 11. DSC data were collected using a TA Instruments Q10 DSC. Typically, samples (~2 mg) were placed in hermetic alodined aluminum sample pans and scanned from 30 to 350° C. at a rate of 10° C./min under a nitrogen purge of 50 mL/min. A Malvern Hydro 2000 SM (A) Mastersizer was used for particle size analysis data using a generic method. Ethyl acetate was used as the dispersant, with a pump speed of 2000 rpm, obstruction of 10-15%. The addition style included direct addition of the solid to the dispersant until desired obstruction is achieved. The number of measurements was a minimum of two. For PSD analysis, a sample was taken from the bulk of the solid. FIGS. 13, 14, and 15 are plots of the PSD analysis for the 30 g, 100 g, and 520 g lots respectively.

TABLE 11

| Physical Characterization | 30 g Lot | 100 g Lot | 520 g Lot |
|---|---|---|---|
| HPLC Analysis | 98.6% | 98.1% | 98.7% |
| DSC, Onset and Peak, ° C. | 176.6, 179.8 | 175.9, 178.6 | 177.3, 178.9 |
| Karl Fisher Titration (wt %) | 1.6 | 1.8 | 2.1 |
| Tap Density | 0.39 g/mL | 0.48 g/mL | 0.49 g/mL |
| Bulk Density | 0.33 g/mL | 0.37 g/mL | 0.39 g/mL |
| Hausner ratio | 1.18 | 1.30 | 1.25 |
| Water Vapor Sorption (gain between 0-50% RH) | 4.2% | 4.1% | 4.2% |
| Particle Size Distribution | DV[10] = 7 μm | DV[10] = 9 μm | DV[10] = 7 μm |
|  | DV[50] = 47 μm | DV[50] = 53 μm | DV[50] = 47 μm |
|  | DV[90] = 92 μm | DV[90] = 109 μm | DV[90] = 93 μm |

Figure 17:
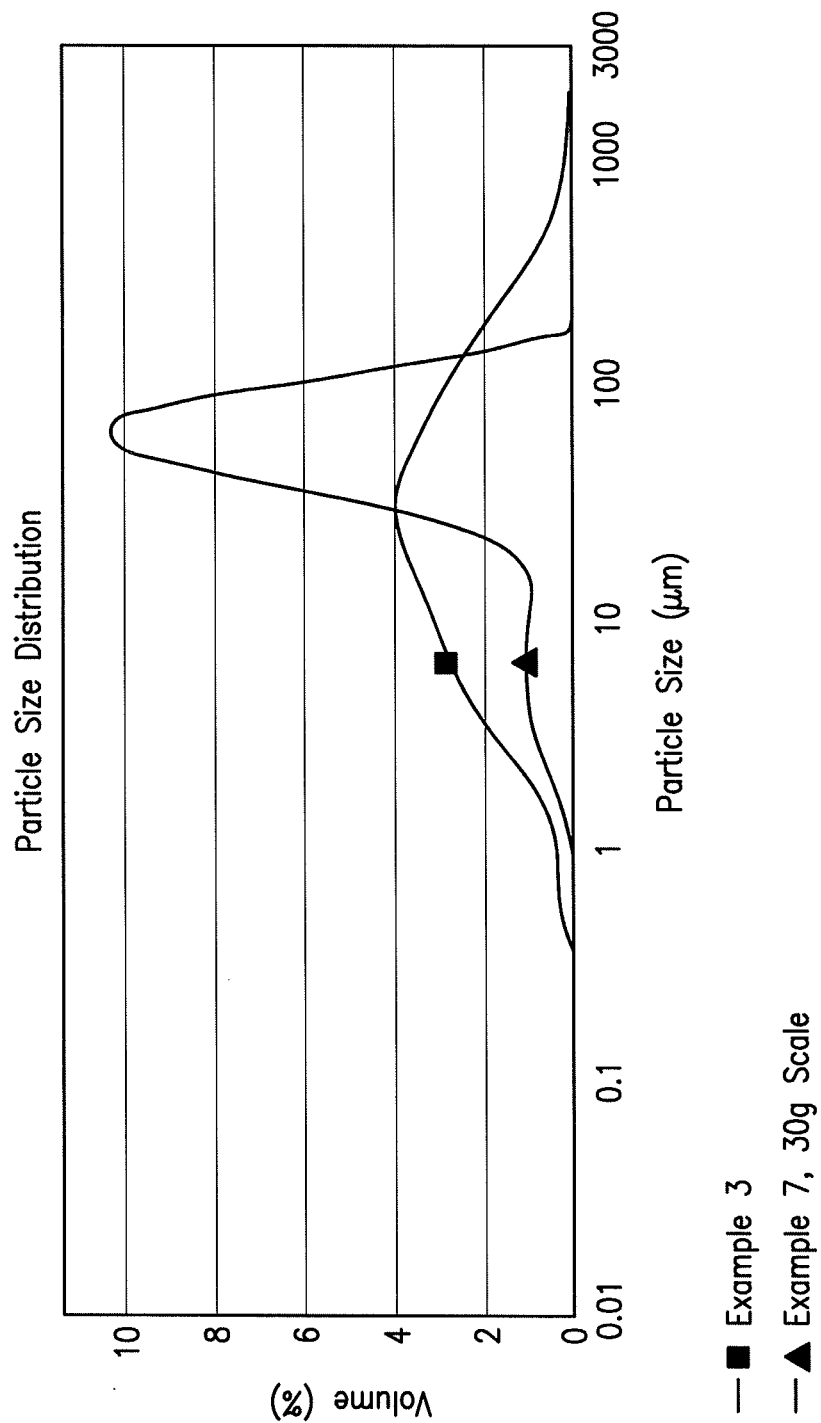
FIG. 17 is a plot of the particle size distribution for the solid α-6-mPEG$_6$-O-hydroxycodone phosphate salts prepared according to Examples 3 and 7.

While previous examples, e.g. Examples 1 and 3, provide a suitable solid phosphate salt, the process of Example 7 produces a crystalline solid that has beneficial characteristics over those previously prepared. For example, the particle size distribution of the solids produced with the present example is narrower than that of solids produced according to Example 3 (See FIG. 17, which compares the PSD of the 30 g example above (Ex. 7) with the process of Example 3). Additionally, the process of Example 3 results in partial oiling of the solid salt, which in turn made the solid salt have waxy characteristics. Additionally, the solids held methanol which may result in extended drying time (in certain cases, up to 7 to 14 days). Furthermore, the previous process also included decantation during the process which can present challenges on a large scale.

In contrast, the process described in the above Example is relatively simple and short. Water was also found to play a role in the solid formation. Water content in the reaction mixture is about 0.4-0.8 wt %, from the aqueous phosphoric acid. The resulting solid is powder like with low tendency of agglomeration upon storage. Compared with the process of Example 3, the product of the new process is more powder like and is more resistant to forming chunks.

Example 8

Preparation of Solid Alpha-6-mPEG$_6$-O-Hydroxycodone Phosphate Salt Tablets

Film coated tablets comprising solid α-6-mPEG$_6$-O-hydroxycodone phosphate prepared according to Example 7 were prepared as follows. Table 12 below reports the components and amount used for the initial blend.

TABLE 12

| Ingredient | Batch Quantity (g) (Target) | Percent (Target) | Actual Amount (g) | Actual Percent |
|---|---|---|---|---|
| solid α-6-mPEG$_6$-O-hydroxycodone phosphate (free base) | 871.875 | 29.54 | 872.00 | 29.53 |
| Dibasic Calcium phosphate anhydrous, NF(Fujicalin ®) | 712.500 | 24.14 | 712.64 | 24.14 |
| Microcrystalline Cellulose (Avicel ® PH102) | 1078.125 | 36.53 | 1078.14 | 36.52 |
| Croscarmellose sodium, USP/NF (Ac-Di-Sol ®) | 127.500 | 4.32 | 127.51 | 4.32 |
| Colloidal Silicon Dioxide, USP/NF (Cabosil ® MP5) | 131.250 | 4.45 | 131.83 | 4.47 |
| Magnesium stearate, NF | 30.000 | 1.02 | 30.01 | 1.02 |
| Total Weight | 2951.25 |  | 2952.13 |  |
| Film coating |  |  |  |  |
| Opadry II White 85F18520 (12% Titanium Dioxide) | 118.050 | 4.00 | — |  |
| Purified water USP | Q.S. |  | Q.S. |  |
| Total Weight | 3069.3 |  |  |  |
| Drug loading (as salt) | 29.54% |  | 29.54% | 29.53 |

A blend was prepared using the actual amounts set forth in Table 12. The solid form of α-6-mPEG$_6$-O-hydroxycodone phosphate, microcrystalline cellulose, and colloidal silicone dioxide were sieved through a mesh #20 sieve and blended using a 4/16 Quart shell V-blender for 15 minutes (Preblend 1). Dibasic calcium phosphate and croscarmellose sodium were sieved through a mesh #20 sieve and transferred with Preblend 1 and blended in 4/16 quart V blender shell and blend it for 15 minutes. Magnesium stearate was sieved through a mesh #40 and added to the blender. The mixture was blended in the 4/16 quart V-blender shell for 3 minutes. The granules formed had a bulk volume of 100 cm³, a tapped volume of 84 cm³, a bulk density of 0.353 g/cm³, a tapped density of 0.420 (g/cm³) and a compressibility index of 15.95%. The appropriate weight of blended granules for each tablet (target dose of 50 mg, 100 mg, 200 mg) was measured into a tablet machine and tablets were formed. Opadry II White 85F18520 was weighed and prepared for coating according to the manufacturer's instructions (dispersion in water). Tablets were sprayed the dispersion until the target weight gain of 4.00% w/w was achieved. Tablets were allowed to cool to room temperature. Table 13 reports data associated with the various tablets made from the blend above (sd=standard deviation).

TABLE 13

|  | 50 mg Tablet | 100 mg Tablet | 200 mg Tablet |
|---|---|---|---|
| Core Tablet | | | |
| Weight (avg) | 196.1 mg (sd = 4.4) | 394.7 mg (sd = 6.7) | 790.6 mg (sd = 9.9) |
| Thickness (avg) | 4.18 mm (sd = 0.01) | 4.56 mm (sd = 0.03) | 6.5 mm (sd = 0.01) |
| Hardness (avg) | 6.1 Kp (sd = 0.4) | 10.0 Kp (sd = 0.36) | 16.00 Kp (sd = 0.46) |
| Disintegration (900 ml H20, 37° C.) | 2:11 (min:sec, sd = 0:31) | 2:58 (min:sec, sd = 0:34) | 1:42 (min:sec, sd = 0:34) |
| Friability | 0.05% | 0.05% | 0.011% |
| Coated Tablet | | | |
| Weight (avg) | 203.9 mg (sd = 4.3) | 404.6 mg (sd = 7.4) | 812.2 mg (sd = 8.3) |
| Thickness (avg) | 4.24 mm (sd = 0.02) | 4.61 mm (sd = 0.06) | 6.64 mm (sd = 0.02) |
| Hardness (avg) | 8.1 Kp (sd = 0.56) | 12.6 Kp (sd = 0.44) | 19.4 Kp (sd = 1.15) |
| Assay | 99.2% | 99.8% | 97.1% |
| Content uniformity (n = 10) | 98.5 ± 1.6 | 97.7 ± 1.7 | 97.5 ± 0.2 |
| RSD | 1.62% | 1.73% | 1.21% |
| Range | 96.8%-101.2% | 95.4%-100.2% | 95.8%-100.2% |

Dissolution data for the tablets prepared as described above are reported in Table 14 below. The dissolution conditions were 0.1N HCl, 900 mL, Type II (paddle) apparatus, 50 RPM.

TABLE 14

| Time (min) | % Dissolved (50 mg tablet) | % Dissolved (100 mg tablet) | % Dissolved (200 mg tablet) |
|---|---|---|---|
| 5 | 43.7 (sd = 9.0) | 33.2 (sd = 13.3) | 21.2 (sd = 9.0) |
| 10 | 94.4 (sd = 2.5) | 77.1 (sd = 7.8) | 60.4 (sd = 2.5) |
| 15 | 95.7 (sd = 2.5) | 91.6 (sd = 2.5) | 82.7 (sd = 2.5) |
| 30 | 96.5 (sd = 2.0) | 92.9 (sd = 2.0) | 93.1 (sd = 2.0) |
| 45 | 97.0 (sd = 2.2) | 93.8 (sd = 1.8) | 93.5 (sd = 2.2) |
| 60 | 98.0 (sd = 1.6) | 94.6 (sd = 1.9) | 94.1 (sd = 1.6) |
| 90 | 98.6 (sd = 1.4) | 96.0 (sd = 1.9) | 95.3 (sd = 1.4) |
| 120 | 98.4 (sd = 1.2) | 96.7 (sd = 1.7) | 96.2 (sd = 1.2) |
| Inf | 98.5 (sd = 1.0) | 98.0 (sd = 1.5) | 98.9 (sd = 1.0) |

Example 9

Preparation of Solid Alpha-6-mPEG$_6$-O-Hydroxycodone Phosphate Salt Tablet

Film coated tablets comprising solid α-6-mPEG$_6$-O-hydroxycodone phosphate prepared according to Example 7 were prepared as follows. Table 14 below reports the components and the targeted amount of each component in the batch and tablets prepared. The actual amounts may slightly vary from the target values.

TABLE 14

| Ingredient | 1300 mg Tablet (mg/tablet) | Batch Quantity (g) |
|---|---|---|
| Intra Granular | | |
| solid α-6-mPEG$_6$-O-hydroxycodone phosphate | 465.00 | 250.38 |
| Dicalcium Phosphate, NF | 444.00 | 239.08 |
| Microcrystalline Cellulose, NF | 219.00 | 117.92 |
| Croscarmellose sodium, NF | 32.00 | 17.23 |
| Colloidal silicon dioxide NF | 54.00 | 29.08 |
| Povidone, USP | 23.00 | 12.38 |
| Purified Water, USP** | Q.S. | Q.S. |
| Total | 1237.00 | 666.07 |
| Extra Granular | | |
| Croscarmellose sodium, USP/NF (Ac-Di-Sol ®) | 32.00 | 17.23 |
| Colloidal silicon dioxide, USP/NF (Cabosil ® MP5) | 15.50 | 8.35 |
| Magnesium stearate | 15.50 | 8.35 |
| Core tablet weight (mg) | 1300.0 | 700.00 |
| Film coating | | |
| Opadry II White 85F18520 (12% Titanium Dioxide) | 52.00 | 28.00 |
| Purified Water, USP** | Q.S. | Q.S. |
| Film coated tablet weight (mg) | 1352.0 | 728.00 |
| Drug loading (as salt) | 35.77% | 35.77% |

Solid α-6-mPEG$_6$-O-hydroxycodone phosphate was placed through a #14 mesh screen followed by colloidal silicone dioxide, and transferred into a high shear granulator. All intragranular excipients (except Povidone) were sieved through a #20 mesh screen, mixed in a V blender for 5 minutes and charged into the high shear granulator. The blend was mixed for 5 minutes with an impeller at (250 rpm) and without chopper. The powder blend was granulated using the Povidone solution (water) with impeller speed of 500 rpm, and the chopper speed of 1200 rpm. The wet granules were transferred to a fluidized bed processor, and dried at an inlet temperature of about 40-50° C. with airflow of about 0.25-0.55 bar. The drying process was continued until the loss on drying (LOD) of granules was <3.00% and the dried granules were passed through a #16 mesh screen. The appropriate weight of granules was loaded and pressed into tablets. The Opadry II White 85F18520 was weighed and the coating dispersion was prepared according to the manufacturer's instructions, which was sprayed onto the tablets until the target weight gain of 4.00% w/w was attained and the tablets were allowed to cool.

Modifications and variations in the subject matter set forth in the above illustrative examples are expected to occur to those skilled in the art. Only such limitations as appear in the appended claims should be placed on any claimed invention.

All publications including books, patents, patent applications and published patent applications cited herein are hereby incorporated by reference in their entireties for all purposes.

What is claimed is:

1. A solid salt form of α-6-mPEG$_6$-O-hydroxycodone phosphate having X-ray powder diffraction peak values comprising: 2.0±0.2, 15.0±0.2, and 17.0±0.2 degrees two theta, when measured with Cu Kα radiation.

2. A method of treating pain in a patient comprising administering the solid salt form of α-6-mPEG$_6$-O-hydroxycodone of claim 1.

3. The method of claim 2, wherein the pain is moderate to severe pain.

4. The method of claim 2, wherein the solid salt form of α-6-mPEG$_6$-O-hydroxycodone is administered as necessary over a 24 hour period to manage moderate to severe pain.

5. A pharmaceutical composition comprising the solid salt form of α-6-mPEG$_6$-O-hydroxycodone of claim 1 and at least one pharmaceutically acceptable excipient.

* * * * *